United States Patent
Nash et al.

(10) Patent No.: US 8,207,304 B2
(45) Date of Patent: Jun. 26, 2012

(54) ANTIBODY ANTAGONISTS OF INTERLEUKIN-13 RECEPTOR α1

(75) Inventors: Andrew Donald Nash, Kew (AU); Louis Jerry Fabri, Diamond Creek (AU); Dennis Zaller, Scotch Plains, NJ (US); William R. Strohl, Bridgewater, NJ (US); Zhiqiang An, Ambler, PA (US)

(73) Assignee: CSL Limited, Parkville (AU)

( * ) Notice: Subject to any disclaimer, the term of this patent is extended or adjusted under 35 U.S.C. 154(b) by 483 days.

(21) Appl. No.: 12/445,759

(22) PCT Filed: Oct. 19, 2007

(86) PCT No.: PCT/US2007/081889
§ 371 (c)(1),
(2), (4) Date: Jul. 13, 2009

(87) PCT Pub. No.: WO2008/049098
PCT Pub. Date: Apr. 24, 2008

(65) Prior Publication Data
US 2009/0285799 A1    Nov. 19, 2009

Related U.S. Application Data

(60) Provisional application No. 60/852,748, filed on Oct. 19, 2006.

(51) Int. Cl.
*C07K 16/00* (2006.01)
*C12N 15/13* (2006.01)

(52) U.S. Cl. .................... 530/387.1; 536/23.53

(58) Field of Classification Search .......... None
See application file for complete search history.

(56) References Cited

U.S. PATENT DOCUMENTS

| | | | |
|---|---|---|---|
| 5,919,456 A | 7/1999 | Puri et al. | 424/181.1 |
| 6,468,528 B1 | 10/2002 | Mak et al. | 424/130.1 |
| 2005/0058645 A1 | 3/2005 | Dunlop et al. | 424/145.1 |
| 2005/0074821 A1 | 4/2005 | Wild, Jr. et al. | 435/7.2 |
| 2006/0075522 A1 | 4/2006 | Cleveland et al. | 800/289 |
| 2006/0177440 A1 | 8/2006 | Siegel | 424/143.1 |
| 2006/0228349 A1 | 10/2006 | Acton et al. | 424/133.1 |

FOREIGN PATENT DOCUMENTS

| | | |
|---|---|---|
| EP | 1449851 A1 | 8/2004 |
| WO | WO 97/15663 | 5/1997 |
| WO | WO 03/046009 | 6/2003 |
| WO | WO 03/080675 | 10/2003 |
| WO | WO 2005/060641 | 7/2005 |
| WO | WO 2006/028197 | 3/2006 |
| WO | WO 2006/055178 A2 | 5/2006 |
| WO | WO 2006/072564 | 7/2006 |

OTHER PUBLICATIONS

Aman et al., "cDNA cloning and characterization of the human interleukin 13 receptor α chain", The Journal of Biological Chemistry 1996 271(46):29265-29270.
Arima et al., "Characterization of the interaction between interleukin-13 and interleukin-13 receptors", The Journal of Biological Chemistry, 2005 280(26):24915-24922.
Akaiwa et al., "Localization of human interleukin 13 receptor in non-haematopoietic cells", Cytokine 2001 13(2):75-84.
Cancino-Diaz et al., "Interleukin-13 receptor in psoriatic keratinocytes:overexpression of the mRNA and underexpression of the protein", J Invest Dermatol 2002 119:1114-1120.
Clement et al., "Monoclonal antibodies against the interleukin-13 receptor α 1 and α 2", Cytokine 1997 9(11):959 Meeting Abstract.
Graber et al., "The distribution of IL-13 receptor α1 expression on B cells, T cells and monocytes and its regulation by IL-13 and IL-4", Eur. J. Immunol. 1998 28:4286-4298.
Hage et al., "Crystal structure of the interleukin-4/receptor α chain complex reveals a mosaic binding interface", Cell 1999 97(2):271-281.
Hilton et al., "Cloning and characterization of a binding subunit of the interleukin 13 receptor that is also a component of the interleukin 4 receptor", Proc Natl Acad Sci USA 1996 93:497-501.
Krause et al., "Blockade of interleukin-13-mediated cell activation by a novel inhibitory antibody to human IL-13 receptor α1", Molecular Immunology 2006 43:1799-1807.
Miloux et al., "Cloning of the human IL-13Rα1 chain and reconstitution with the IL-4Rα of a functional IL-4/IL-13 receptor complex", FEBS Letter 1997 401:163-166.
Ogata et al., "Regulation of interleukin-13 receptor constituents on mature human B lymphocytes", The Journal of Biological Chemistry 1998 273(16):9864-9871.
Poudrier et al., "A novel monoclonal antibody, C41, reveals IL-13Rα1 expression by murine germinal center B cells and follicular dendritic cells", Eur. J. Immunol. 2000 30:3157-31634.
Wells et al., Hematopoietic receptor complexes, Ann Rev Biochem 1996 65:609-634.
C. Vermont-Desroches et al., "Identification and characterization of Abs anti-IL-13Rα1 and IL-13Rα2", Tissue Antigens 2000 5(suppl):52-53 Meeting Abstract.
NCBI Accession No. NP_001551 [gi:4504647] with revision history—Mar. 19, 1999-Nov. 17, 2006.

(Continued)

*Primary Examiner* — Michael Pak
(74) *Attorney, Agent, or Firm* — Licata & Tyrrell P.C.

(57) ABSTRACT

Antibody antagonists of human interleukin-13 receptor alpha 1 are disclosed. The antibody molecules are useful in the inhibition of IL-13Rα1-mediated activities and, accordingly, present desirable antagonists for the use in the treatment of conditions associated with hIL-13Rα activity. The present invention also discloses nucleic acid encoding said antibody molecules, vectors, host cells, and compositions comprising the antibody molecules. Methods of using the antibody molecules for inhibiting or antagonizing IL-13Rα1-mediated activities are also disclosed.

6 Claims, 2 Drawing Sheets

OTHER PUBLICATIONS

NCBI Accession No. O09030 [gi:2494719] with revision history Feb. 1, 1997-Nov. 28, 2006.

NCBI Accession No. U62858 [gi:1695875] with revision history Dec. 1, 1996-Mar. 9, 2000.

NCBI Accession No. AAP78901 [gi:32264958] with revision history—Jul. 1, 2003.

NCBI Accession No. CAA78508 [gi:7345] with revision history Dec. 3, 1992-Apr. 18, 2005.

Li et al., "Effects of Th2 cytokines on chemokine expression in the lung: IL-13 potently induces eotaxin expression by airway epithelial cells", Journal of Immunology 1999 162:2477-2487.

Extended Search Report from EP Application No. 07854205.7 filed Oct. 19, 2007, Jun. 1, 2010, EPO.

```
                |--- CH1 STARTS HERE
IgG1    LVTVSSASTK GPSVFPLAPS SKSTSGGTAA LGCLVKDYFP EPVTVSWNSG
IgG2    LVTVSSASTK GPSVFPLAPC SRSTSESTAA LGCLVKDYFP EPVTVSWNSG
IgG4    LVTVSSASTK GPSVFPLAPC SRSTSESTAA LGCLVKDYFP EPVTVSWNSG
IgG2M4  LVTVSSASTK GPSVFPLAPC SRSTSESTAA LGCLVKDYFP EPVTVSWNSG
        (VH-C1 LINKER)
                                          C200
IgG1    ALTSGVHTFP AVLQSSGLYS LSSVVTVPSS SLGTQTYICN VNHKPSNTKV
IgG2    ALTSGVHTFP AVLQSSGLYS LSSVVTVTSS NFGTQTYTCN VDHKPSNTKV
IgG4    ALTSGVHTFP AVLQSSGLYS LSSVVTVPSS SLGTKTYTCN VDHKPSNTKV
IgG2M4  ALTSGVHTFP AVLQSSGLYS LSSVVTVTSS NFGTQTYTCN VDHKPSNTKV

-HINGE REGION--||----CH2-> P238              M252     C261
IgG1    DKKAEPKSCD KTHTCPPCPA PELLGGPSVF LFPPKPKDTL MISRTPEVTC
IgG2    DKTVERKCC- --VECPPCPA PP-VAGPSVF LFPPKPKDTL MISRTPEVTC
IgG4    DKRVESKYGP ---PCPSCPA PEFLGGPSVF LFPPKPKDTL MISRTPEVTC
IgG2M4  DKTVERKCC- --VECPPCPA PP-VAGPSVF LFPPKPKDTL MISRTPEVTC
                           (LOWER HINGE)              FcRn-BIND

D265 D270                          N297*     T307
IgG1    VVVDVSHEDP EVKFNWYVDG VEVHNAKTKP REEQYNSTYR VVSVLTVLHQ
IgG2    VVVDVSHEDP EVQFNWYVDG VEVHNAKTKP REEQFNSTFR VVSVLTVVHQ
IgG4    VVVDVSQEDP EVQFNWYVDG VEVHNAKTKP REEQFNSTYR VVSVLTVLHQ
IgG2M4  VVVDVSQEDP EVQFNWYVDG VEVHNAKTKP REEQFNSTFR VVSVLTVLHQ
        B/C LOOP                          C'E LOOP  FcRn-BIND

C321      P329          |----CH3->
IgG1    DWLNGKEYKC KVSNKALPAPI EKTISKAKG QPREPQVYTL PPSRDELTKN
IgG2    DWLNGKEYKC KVSNKGLPAPI EKTISKTKG QPREPQVYTL PPSREEMTKN
IgG4    DWLNGKEYKC KVSNKGLPSSI EKTISKAKG QPREPQVYTL PPSQEEMTKN
IgG2M4  DWLNGKEYKC KVSNKGLPSSI EKTISKTKG QPREPQVYTL PPSREEMTKN
                      F/G LOOP

IgG1    QVSLTCLVKG FYPSDIAVEW ESNGQPENNY KTTPPVLDSD GSFFLYSKLT
IgG2    QVSLTCLVKG FYPSDIAVEW ESNGQPENNY KTTPPMLDSD GSFFLYSKLT
IgG4    QVSLTCLVKG FYPSDIAVEW ESNGQPENNY KTTPPVLDSD GSFFLYSRLT
IgG2M4  QVSLTCLVKG FYPSDIAVEW ESNGQPENNY KTTPPMLDSD GSFFLYSKLT

H433
IgG1    VDKSRWQQGN VFSCSVMHEA LHNHYTQKSL SLSPGK* (SEQ ID NO:75)
IgG2    VDKSRWQQGN VFSCSVMHEA LHNHYTQKSL SLSPGK* (SEQ ID NO:76)
IgG4    VDKSRWQEGN VFSCSVMHEA LHNHYTQKSL SLSLGK* (SEQ ID NO:77)
IgG2M4  VDKSRWQQGN VFSCSVMHEA LHNHYTQKSL SLSPGK* (SEQ ID NO:78)
                             FcRn-BIND
```

FIG. 2

SEQUENCE LISTING

```
<160> NUMBER OF SEQ ID NOS: 84

<210> SEQ ID NO 1
<211> LENGTH: 121
<212> TYPE: PRT
<213> ORGANISM: Homo sapiens

<400> SEQUENCE: 1

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Tyr Tyr
                20                  25                  30

Gly Met His Trp Val Arg Gln Ala Pro Gly Lys Gly Leu Glu Trp Val
            35                  40                  45

Ala Phe Ile Trp Tyr Asp Gly Ser Asn Lys Tyr Tyr Glu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Ala Ala Gly Ala Val Glu Tyr Phe Gln His Trp Gly
            100                 105                 110

Gln Gly Thr Leu Val Thr Val Ser Ser
        115                 120

<210> SEQ ID NO 2
<211> LENGTH: 10
<212> TYPE: PRT
<213> ORGANISM: Homo sapiens

<400> SEQUENCE: 2

Gly Phe Thr Phe Ser Tyr Tyr Gly Met His
1               5                   10

<210> SEQ ID NO 3
<211> LENGTH: 17
<212> TYPE: PRT
<213> ORGANISM: Homo sapiens

<400> SEQUENCE: 3

Phe Ile Trp Tyr Asp Gly Ser Asn Lys Tyr Tyr Glu Asp Ser Val Lys
1               5                   10                  15

Gly

<210> SEQ ID NO 4
<211> LENGTH: 12
<212> TYPE: PRT
<213> ORGANISM: Homo sapiens

<400> SEQUENCE: 4

Val Ala Ala Ala Gly Ala Val Glu Tyr Phe Gln His
1               5                   10

<210> SEQ ID NO 5
<211> LENGTH: 107
<212> TYPE: PRT
```

-continued

<213> ORGANISM: Homo sapiens

<400> SEQUENCE: 5

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Val Ile Ser Ser Val
            20                  25                  30

Leu Ala Trp Tyr Gln Gln Lys Ser Gly Lys Gly Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 6
<211> LENGTH: 11
<212> TYPE: PRT
<213> ORGANISM: Homo sapiens

<400> SEQUENCE: 6

Arg Ala Ser Gln Val Ile Ser Ser Val Leu Ala
1               5                   10

<210> SEQ ID NO 7
<211> LENGTH: 7
<212> TYPE: PRT
<213> ORGANISM: Homo sapiens

<400> SEQUENCE: 7

Asp Ala Ser Ser Leu Glu Ser
1               5

<210> SEQ ID NO 8
<211> LENGTH: 9
<212> TYPE: PRT
<213> ORGANISM: Homo sapiens

<400> SEQUENCE: 8

Gln Gln Phe Asn Ser Tyr Pro Leu Thr
1               5

<210> SEQ ID NO 9
<211> LENGTH: 128
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Ala Ile Trp Tyr Asp Gly Ser Asp Lys Asn Tyr Ala Asp Ser Val
50                  55                  60

Lys Gly Arg Val Thr Ile Ser Arg Asp Thr Ser Lys Lys Thr Leu Tyr
65                  70                  75                  80

Leu Gln Met Asn Ser Leu Arg Ala Glu Asp Thr Ala Ile Tyr Tyr Cys
                    85                  90                  95

Ala Arg Glu Ile Thr Ile Met Arg Gly Leu Ile Lys Asn Tyr Tyr Tyr
            100                 105                 110

Tyr Gly Met Asp Val Trp Gly Gln Gly Thr Thr Val Thr Val Ser Ser
        115                 120                 125

<210> SEQ ID NO 10
<211> LENGTH: 10
<212> TYPE: PRT
<213> ORGANISM: Homo sapiens

<400> SEQUENCE: 10

Gly Phe Thr Phe Ser Asn Tyr Gly Met His
1               5                   10

<210> SEQ ID NO 11
<211> LENGTH: 17
<212> TYPE: PRT
<213> ORGANISM: Homo sapiens

<400> SEQUENCE: 11

Ala Ile Trp Tyr Asp Gly Ser Asp Lys Asn Tyr Ala Asp Ser Val Lys
1               5                   10                  15

Gly

<210> SEQ ID NO 12
<211> LENGTH: 19
<212> TYPE: PRT
<213> ORGANISM: Homo sapiens

<400> SEQUENCE: 12

Glu Ile Thr Ile Met Arg Gly Leu Ile Lys Asn Tyr Tyr Tyr Tyr Gly
1               5                   10                  15

Met Asp Val

<210> SEQ ID NO 13
<211> LENGTH: 118
<212> TYPE: PRT
<213> ORGANISM: Homo sapiens

<400> SEQUENCE: 13

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Leu Thr Trp Val Arg Gln Ala Pro Gly Lys Gly Leu Glu Trp Val
        35                  40                  45

Ser Thr Ile Ser Gly Arg Gly Tyr Ser Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Glu Glu Gly His Trp Phe Phe Asp Val Trp Gly Arg Gly Thr
            100                 105                 110

Leu Val Thr Val Ser Ser
        115

-continued

```
<210> SEQ ID NO 14
<211> LENGTH: 10
<212> TYPE: PRT
<213> ORGANISM: Homo sapiens

<400> SEQUENCE: 14

Gly Phe Thr Phe Asn Asn Tyr Ala Leu Thr
1               5                   10

<210> SEQ ID NO 15
<211> LENGTH: 17
<212> TYPE: PRT
<213> ORGANISM: Homo sapiens

<400> SEQUENCE: 15

Thr Ile Ser Gly Arg Gly Tyr Ser Ile Tyr Tyr Ala Asp Ser Val Lys
1               5                   10                  15

Gly

<210> SEQ ID NO 16
<211> LENGTH: 9
<212> TYPE: PRT
<213> ORGANISM: Homo sapiens

<400> SEQUENCE: 16

Glu Glu Gly His Trp Phe Phe Asp Val
1               5

<210> SEQ ID NO 17
<211> LENGTH: 107
<212> TYPE: PRT
<213> ORGANISM: Homo sapiens

<400> SEQUENCE: 17

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Tyr
                85                  90                  95

Thr Phe Gly Gln Gly Thr Lys Leu Glu Ile Lys
            100                 105

<210> SEQ ID NO 18
<211> LENGTH: 11
<212> TYPE: PRT
<213> ORGANISM: Homo sapiens

<400> SEQUENCE: 18

Arg Ala Ser Gln Ser Ile Gly Ser Ser Leu His
1               5                   10

<210> SEQ ID NO 19
<211> LENGTH: 7
<212> TYPE: PRT
<213> ORGANISM: Homo sapiens
```

```
<400> SEQUENCE: 19

Tyr Ala Ser Gln Ser Phe Ser
1               5

<210> SEQ ID NO 20
<211> LENGTH: 9
<212> TYPE: PRT
<213> ORGANISM: Homo sapiens

<400> SEQUENCE: 20

His Gln Ser Ser Ser Leu Pro Tyr Thr
1               5

<210> SEQ ID NO 21
<211> LENGTH: 118
<212> TYPE: PRT
<213> ORGANISM: Homo sapiens

<400> SEQUENCE: 21

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Thr Ile Ser Gly Arg Gly Tyr Ser Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Glu Glu Gly His Trp Tyr Phe Asp Val Trp Gly Arg Gly Thr
            100                 105                 110

Leu Val Thr Val Ser Ser
        115

<210> SEQ ID NO 22
<211> LENGTH: 10
<212> TYPE: PRT
<213> ORGANISM: Homo sapiens

<400> SEQUENCE: 22

Gly Phe Thr Phe Ser Asn Tyr Ala Met Thr
1               5                   10

<210> SEQ ID NO 23
<211> LENGTH: 9
<212> TYPE: PRT
<213> ORGANISM: Homo sapiens

<400> SEQUENCE: 23

Glu Glu Gly His Trp Tyr Phe Asp Val
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic 8B4-78M VL CDR3

<400> SEQUENCE: 24
```

```
Met Ser Ser Met Gly Leu Pro Tyr Thr
1               5
```

<210> SEQ ID NO 25
<211> LENGTH: 9
<212> TYPE: PRT
<213> ORGANISM: Artificial sequence
<220> FEATURE:
<223> OTHER INFORMATION: Synthetic 8B4-82 VL CDR3

<400> SEQUENCE: 25

```
Ala Ser Ser Arg Gly Leu Pro Tyr Thr
1               5
```

<210> SEQ ID NO 26
<211> LENGTH: 9
<212> TYPE: PRT
<213> ORGANISM: Artificial sequence
<220> FEATURE:
<223> OTHER INFORMATION: Synthetic 8B4-18C VL CDR3

<400> SEQUENCE: 26

```
Met Asn Ser Leu Gly Leu Pro Tyr Thr
1               5
```

<210> SEQ ID NO 27
<211> LENGTH: 9
<212> TYPE: PRT
<213> ORGANISM: Artificial sequence
<220> FEATURE:
<223> OTHER INFORMATION: Synthetic 8B4-36 VL CDR3

<400> SEQUENCE: 27

```
Val Ser Ser Trp Gly Leu Pro Tyr Thr
1               5
```

<210> SEQ ID NO 28
<211> LENGTH: 9
<212> TYPE: PRT
<213> ORGANISM: Artificial sequence
<220> FEATURE:
<223> OTHER INFORMATION: Synthetic 8B4-21C VL CDR3

<400> SEQUENCE: 28

```
Lys Ser Ser Ala Gly Leu Pro Tyr Thr
1               5
```

<210> SEQ ID NO 29
<211> LENGTH: 9
<212> TYPE: PRT
<213> ORGANISM: Artificial sequence
<220> FEATURE:
<223> OTHER INFORMATION: Synthetic 8B4-74C VL CDR3

<400> SEQUENCE: 29

```
Met Ser Ser Leu Gly Leu Pro Tyr Thr
1               5
```

<210> SEQ ID NO 30
<211> LENGTH: 363
<212> TYPE: DNA
<213> ORGANISM: Homo sapiens

<400> SEQUENCE: 30

```
caggtgcagc tggtggagtc tgggggaggc gtggtccagc ctggggaggtc cctgagactc    60 tcctgtgcag cgtctggatt caccttcagt tactatggca tgcactgggt ccgccaggct   120
```

```
ccaggcaagg ggctggagtg ggtggcattt atatggtatg atggaagtaa taaatattat    180
gaagactccg tgaagggccg attcaccatc tccagagaca attccaagaa cacgctgtat    240
ctgcaaatga acagcctgag agccgaggac acggctgtgt attactgtgc gagggtagca    300
gcagctggtc tgttgaata cttccagcac tggggccagg gcaccctggt caccgtctcc    360
tca                                                                  363

<210> SEQ ID NO 31
<211> LENGTH: 30
<212> TYPE: DNA
<213> ORGANISM: Homo sapiens

<400> SEQUENCE: 31
ggattcacct tcagttacta tggcatgcac                                      30

<210> SEQ ID NO 32
<211> LENGTH: 51
<212> TYPE: DNA
<213> ORGANISM: Homo sapiens

<400> SEQUENCE: 32
tttatatggt atgatggaag taataaatat tatgaagact ccgtgaaggg c               51

<210> SEQ ID NO 33
<211> LENGTH: 36
<212> TYPE: DNA
<213> ORGANISM: Homo sapiens

<400> SEQUENCE: 33
gtagcagcag ctggtgctgt tgaatacttc cagcac                               36

<210> SEQ ID NO 34
<211> LENGTH: 321
<212> TYPE: DNA
<213> ORGANISM: Homo sapiens

<400> SEQUENCE: 34
gccatccagt tgacccagtc tccatcctcc ctgtctgcat ctgtaggaga cagagtcacc     60
atcacttgcc gggcaagtca ggtcattagc agtgttttag cctggtatca gcagaaatca    120
gggaaaggtc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctctcac tttcggcgga    300
gggaccaagg tggagatcaa a                                               321

<210> SEQ ID NO 35
<211> LENGTH: 33
<212> TYPE: DNA
<213> ORGANISM: Homo sapiens

<400> SEQUENCE: 35
cgggcaagtc aggtcattag cagtgtttta gcc                                  33

<210> SEQ ID NO 36
<211> LENGTH: 21
<212> TYPE: DNA
<213> ORGANISM: Homo sapiens

<400> SEQUENCE: 36
gatgcctcca gtttggaaag t                                               21
```

<210> SEQ ID NO 37
<211> LENGTH: 27
<212> TYPE: DNA
<213> ORGANISM: Homo sapiens

<400> SEQUENCE: 37
caacagttta atagttaccc tctcact                                27

<210> SEQ ID NO 38
<211> LENGTH: 384
<212> TYPE: DNA
<213> ORGANISM: Homo sapiens

<400> SEQUENCE: 38
caggtgcagc tggtggagtc tgggggaggc gtggtccagc ctgggaggtc cctgagactc    60
tcctgtgcag cgtctggatt caccttcagt aattatggca tgcactgggt ccgccaggct   120
ccaggcaagg ggctggagtg gtggcggca atttggtatg atggaagtga aaaaactat    180 gcagactccg tgaagggccg agtcaccatc tccagagaca cctccaagaa aacgttgtat   240
ctgcaaatga acagtctgag agccgaggac acggctatat actactgtgc gagagagatt   300
actataatgc gggacttat taaaaactac tactattatg gtatggacgt ctggggccaa    360
gggaccacgg tcaccgtctc ctca                                         384

<210> SEQ ID NO 39
<211> LENGTH: 30
<212> TYPE: DNA
<213> ORGANISM: Homo sapiens

<400> SEQUENCE: 39
ggattcacct tcagtaatta tggcatgcac                                30

<210> SEQ ID NO 40
<211> LENGTH: 51
<212> TYPE: DNA
<213> ORGANISM: Homo sapiens

<400> SEQUENCE: 40
gcaatttggt atgatggaag tgataaaaac tatgcagact ccgtgaaggg c         51

<210> SEQ ID NO 41
<211> LENGTH: 44
<212> TYPE: DNA
<213> ORGANISM: Homo sapiens

<400> SEQUENCE: 41
gagattacta atgcggggg acttattaaa aactactact atta                 44

<210> SEQ ID NO 42
<211> LENGTH: 354
<212> TYPE: DNA
<213> ORGANISM: Homo sapiens

<400> SEQUENCE: 42
gaggtgcagg tgttggagtc tgggggaggc ttggtacagc ctgggggtc cctgagactc    60 tcctgtgcag cctctggatt cacctttaac aactatgcct tgacctgggt ccgccaggct   120
ccagggaagg ggctggagtg gtctcaact attagtggtc gtggttatag tatatactac   180
gcagactccg tgaagggccg gttcaccatc tccagagaca attccaagaa cacggtgtat   240
ctgcaaatga acagcctgag agccgaggac acggccgtat attactgtgc gaaagaggaa   300

```
gggcactggt tcttcgatgt ctggggccgt ggcaccctgg tcactgtctc ctca         354
```

<210> SEQ ID NO 43
<211> LENGTH: 30
<212> TYPE: DNA
<213> ORGANISM: Homo sapiens

<400> SEQUENCE: 43

```
ggattcacct ttaacaacta tgccttgacc                                    30
```

<210> SEQ ID NO 44
<211> LENGTH: 51
<212> TYPE: DNA
<213> ORGANISM: Homo sapiens

<400> SEQUENCE: 44

```
actattagtg gtcgtggtta tagtatatac tacgcagact ccgtgaaggg c             51
```

<210> SEQ ID NO 45
<211> LENGTH: 35
<212> TYPE: DNA
<213> ORGANISM: Homo sapiens

<400> SEQUENCE: 45

```
gaggaagggc actggttctt cgatgtctgg ggccg                              35
```

<210> SEQ ID NO 46
<211> LENGTH: 321
<212> TYPE: DNA
<213> ORGANISM: Homo sapiens

<400> SEQUENCE: 46

```
gaaattgtgc tgactcagtc tccagacttt cagtctgtga ctccaaagga gaaagtcacc    60
atcacctgcc gggccagtca gagcattggt agtagcttac actggtacca gcagaaacca   120
gatcagtctc caaagctcct catcaagtat gcttcccagt ccttctcagg ggtcccctcg   180
aggttcagtg gcagtggatc tgggacagat ttcaccctca ccatcaatag cctggaagct   240
gaagatgctg cagcgtatta ctgtcatcag agtagtagtt taccgtacac ttttggccag   300
gggaccaagc tggagatcaa a                                             321
```

<210> SEQ ID NO 47
<211> LENGTH: 33
<212> TYPE: DNA
<213> ORGANISM: Homo sapiens

<400> SEQUENCE: 47

```
cgggccagtc agagcattgg tagtagctta cac                                33
```

<210> SEQ ID NO 48
<211> LENGTH: 21
<212> TYPE: DNA
<213> ORGANISM: Homo sapiens

<400> SEQUENCE: 48

```
tatgcttccc agtccttctc a                                             21
```

<210> SEQ ID NO 49
<211> LENGTH: 27
<212> TYPE: DNA
<213> ORGANISM: Homo sapiens

<400> SEQUENCE: 49

```
catcagagta gtagtttacc gtacact                                        27
```

<210> SEQ ID NO 50
<211> LENGTH: 354
<212> TYPE: DNA
<213> ORGANISM: Homo sapiens

<400> SEQUENCE: 50

```
gaggtgcagg tgttggagtc tgggggaggc ttggtacagc ctggggggtc cctgagactc    60
tcctgtgcag cctctggatt cacctttagc aactatgcca tgacctgggt ccgccaggct   120
ccagggaagg gctggagtg gtctcaact attagtggtc gtggttatag tatatactac    180
gcagactccg tgaagggccg gttcaccatc tccagagaca attccaagaa cacggtgtat   240
ctgcaaatga acagcctgag agccgaggac acggccgtat attactgtgc gaaagaggaa   300
ggtcactggt acttcgatgt ctggggccgt ggcaccctgg tcactgtctc ctca         354
```

<210> SEQ ID NO 51
<211> LENGTH: 30
<212> TYPE: DNA
<213> ORGANISM: Homo sapiens

<400> SEQUENCE: 51

```
ggattcacct ttagcaacta tgccatgacc                                     30
```

<210> SEQ ID NO 52
<211> LENGTH: 27
<212> TYPE: DNA
<213> ORGANISM: Homo sapiens

<400> SEQUENCE: 52

```
gaggaaggtc actggtactt cgatgtc                                        27
```

<210> SEQ ID NO 53
<211> LENGTH: 107
<212> TYPE: PRT
<213> ORGANISM: Artificial sequence
<220> FEATURE:
<223> OTHER INFORMATION: Synthetic 8B4-78M VL

<400> SEQUENCE: 53

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Met Ser Ser Met Gly Leu Pro Tyr
                85                  90                  95

Thr Phe Gly Gln Gly Thr Lys Leu Glu Ile Lys
            100                 105
```

<210> SEQ ID NO 54
<211> LENGTH: 107
<212> TYPE: PRT
<213> ORGANISM: Artificial sequence
<220> FEATURE:
<223> OTHER INFORMATION: Synthetic 8B4-82 VL

```
<400> SEQUENCE: 54

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Ala Ser Ser Arg Gly Leu Pro Tyr
                85                  90                  95

Thr Phe Gly Gln Gly Thr Lys Leu Glu Ile Lys
            100                 105

<210> SEQ ID NO 55
<211> LENGTH: 107
<212> TYPE: PRT
<213> ORGANISM: Artificial sequence
<220> FEATURE:
<223> OTHER INFORMATION: Synthetic 8B4-18C VL

<400> SEQUENCE: 55

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Met Asn Ser Leu Gly Leu Pro Tyr
                85                  90                  95

Thr Phe Gly Gln Gly Thr Lys Leu Glu Ile Lys
            100                 105

<210> SEQ ID NO 56
<211> LENGTH: 107
<212> TYPE: PRT
<213> ORGANISM: Artificial sequence
<220> FEATURE:
<223> OTHER INFORMATION: Synthetic 8B4-36 VL

<400> SEQUENCE: 56

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80
```

```
Glu Asp Ala Ala Ala Tyr Tyr Cys Val Ser Ser Trp Gly Leu Pro Tyr
                85                  90                  95

Thr Phe Gly Gln Gly Thr Lys Leu Glu Ile Lys
            100                 105
```

<210> SEQ ID NO 57
<211> LENGTH: 107
<212> TYPE: PRT
<213> ORGANISM: Artificial sequence
<220> FEATURE:
<223> OTHER INFORMATION: Synthetic 8B4-21C VL

<400> SEQUENCE: 57

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Lys Ser Ser Ala Gly Leu Pro Tyr
                85                  90                  95

Thr Phe Gly Gln Gly Thr Lys Leu Glu Ile Lys
            100                 105
```

<210> SEQ ID NO 58
<211> LENGTH: 107
<212> TYPE: PRT
<213> ORGANISM: Artificial sequence
<220> FEATURE:
<223> OTHER INFORMATION: Synthetic 8B4-74C VL

<400> SEQUENCE: 58

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Met Ser Ser Leu Gly Leu Pro Tyr
                85                  90                  95

Thr Phe Gly Gln Gly Thr Lys Leu Glu Ile Lys
            100                 105
```

<210> SEQ ID NO 59
<211> LENGTH: 100
<212> TYPE: DNA
<213> ORGANISM: Artificial sequence
<220> FEATURE:
<223> OTHER INFORMATION: Synthetic 8B4 VL forward primer

<400> SEQUENCE: 59
atcgaagctt gccgccacca tgagtgtgcc cactcaggtc ctggggttgc tgctgctgtg    60

-continued

```
gcttacagat gccagatgtg aaattgtgct gactcagtct                         100
```

<210> SEQ ID NO 60
<211> LENGTH: 22
<212> TYPE: DNA
<213> ORGANISM: Artificial sequence
<220> FEATURE:
<223> OTHER INFORMATION: Synthetic 8B4 VL reverse primer

<400> SEQUENCE: 60

```
ccaccgtacg tttgatttcc ac                                            22
```

<210> SEQ ID NO 61
<211> LENGTH: 99
<212> TYPE: DNA
<213> ORGANISM: Artificial sequence
<220> FEATURE:
<223> OTHER INFORMATION: Synthetic 8B4 VH forward primer

<400> SEQUENCE: 61

```
gcactgaagc ttgccgccac catggaatgg agctgggtct ttctcttctt cctgtcagta   60
actacaggtg tccactccga ggtgcaggtg ttggagtct                          99
```

<210> SEQ ID NO 62
<211> LENGTH: 26
<212> TYPE: DNA
<213> ORGANISM: Artificial sequence
<220> FEATURE:
<223> OTHER INFORMATION: Synthetic 8B4 VH reverse primer

<400> SEQUENCE: 62

```
agaccgatgg gcccttggtg gaggct                                        26
```

<210> SEQ ID NO 63
<211> LENGTH: 9
<212> TYPE: PRT
<213> ORGANISM: Artificial sequence
<220> FEATURE:
<223> OTHER INFORMATION: Synthetic 8B4-80C VL CDR3

<400> SEQUENCE: 63

Met Ser Ser Trp Gly Leu Pro Tyr Thr
1               5

<210> SEQ ID NO 64
<211> LENGTH: 107
<212> TYPE: PRT
<213> ORGANISM: Artificial sequence
<220> FEATURE:
<223> OTHER INFORMATION: Synthetic 8B4-80C VL

<400> SEQUENCE: 64

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Met Ser Ser Trp Gly Leu Pro Tyr
                85                  90                  95

Thr Phe Gly Gln Gly Thr Lys Leu Glu Ile Lys
            100              105

<210> SEQ ID NO 65
<211> LENGTH: 27
<212> TYPE: DNA
<213> ORGANISM: Artificial sequence
<220> FEATURE:
<223> OTHER INFORMATION: Synthetic 8B4-78 M VL CDR3 nucleic acid

<400> SEQUENCE: 65
atgtcgtcga tgggtttacc gtacact                                          27

<210> SEQ ID NO 66
<211> LENGTH: 321
<212> TYPE: DNA
<213> ORGANISM: Artificial sequence
<220> FEATURE:
<223> OTHER INFORMATION: Synthetic 8B4-78M VL nucleic acid

<400> SEQUENCE: 66
gaaattgtgc tgactcagtc tccagacttt cagtctgtga ctccaaagga gaaagtcacc      60
atcacctgcc gggccagtca gagcattggt agtagcttac actggtacca gcagaaacca     120
gatcagtctc caaaactcct catcaagtat gcttcccagt cctttctcagg ggtcccctcg    180 aggttcagtg gcagtggatc tgggacagat ttcaccctca ccatcaatag cctggaagct     240
gaagatgctg cagcgtatta ctgtatgtcg tcgatgggtt taccgtacac ttttggccag     300
gggaccaagc tggagatcaa a                                               321

<210> SEQ ID NO 67
<211> LENGTH: 27
<212> TYPE: DNA
<213> ORGANISM: Artificial sequence
<220> FEATURE:
<223> OTHER INFORMATION: Synthetic 8B4-82 VL CDR3 nucleic acid

<400> SEQUENCE: 67
gctagtagtc gggggttacc gtacact                                          27

<210> SEQ ID NO 68
<211> LENGTH: 321
<212> TYPE: DNA
<213> ORGANISM: Artificial sequence
<220> FEATURE:
<223> OTHER INFORMATION: Synthetic 8B4-82 VL nucleic acid

<400> SEQUENCE: 68
gaaattgtgc tgactcagtc tccagacttt cagtctgtga ctccaaagga gaaagtcacc      60
atcacctgcc gggccagtca gagcattggt agtagcttac actggtacca gcagaaacca     120
gatcagtctc caaaactcct catcaagtat gcttcccagt cctttctcagg ggtcccctcg    180 aggttcagtg gcagtggatc tgggacagat ttcaccctca ccatcaatag cctggaagct     240
gaagatgctg cagcgtatta ctgtgctagt agtcgggggt taccgtacac ttttggccag     300
gggaccaagc tggagatcaa a                                               321

<210> SEQ ID NO 69
<211> LENGTH: 27
<212> TYPE: DNA
<213> ORGANISM: Artificial sequence
<220> FEATURE:
<223> OTHER INFORMATION: Synthetic 8B4-18C VL CDR3 nucleic acid

```
<400> SEQUENCE: 69
atgaattctt tggggttacc gtacact                                              27

<210> SEQ ID NO 70
<211> LENGTH: 321
<212> TYPE: DNA
<213> ORGANISM: Artificial sequence
<220> FEATURE:
<223> OTHER INFORMATION: Synthetic 8B4-18C VL nucleic acid

<400> SEQUENCE: 70
gaaattgtgc tgactcagtc tccagacttt cagtctgtga ctccaaagga gaaagtcacc          60
atcacctgcc gggccagtca gagcattggt agtagcttac actggtacca gcagaaacca         120
gatcagtctc caaaactcct catcaagtat gcttcccagt ccttctcagg ggtcccctcg         180
aggttcagtg gcagtggatc tgggacagat ttcaccctca ccatcaatag cctggaagct         240
gaagatgctg cagcgtatta ctgtatgaat tctttggggt taccgtacac ttttggccag         300
gggaccaagc tggagatcaa a                                                  321

<210> SEQ ID NO 71
<211> LENGTH: 27
<212> TYPE: DNA
<213> ORGANISM: Artificial sequence
<220> FEATURE:
<223> OTHER INFORMATION: Synthetic 8B4-36 VL CDR3 nucleic acid

<400> SEQUENCE: 71
gtttcgtctt gggggttacc gtacact                                              27

<210> SEQ ID NO 72
<211> LENGTH: 321
<212> TYPE: DNA
<213> ORGANISM: Artificial sequence
<220> FEATURE:
<223> OTHER INFORMATION: Synthetic 8B4-36 VL nucleic acid

<400> SEQUENCE: 72
gaaattgtgc tgactcagtc tccagacttt cagtctgtga ctccaaagga gaaagtcacc          60
atcacctgcc gggccagtca gagcattggt agtagcttac actggtacca gcagaaacca         120
gatcagtctc caaaactcct catcaagtat gcttcccagt ccttctcagg ggtcccctcg         180
aggttcagtg gcagtggatc tgggacagat ttcaccctca ccatcaatag cctggaagct         240
gaagatgctg cagcgtatta ctgtgtttcg tcttgggggt taccgtacac ttttggccag         300
gggaccaagc tggagatcaa a                                                  321

<210> SEQ ID NO 73
<211> LENGTH: 27
<212> TYPE: DNA
<213> ORGANISM: Artificial sequence
<220> FEATURE:
<223> OTHER INFORMATION: Synthetic 8B4-74C VL CDR3 nucleic acid

<400> SEQUENCE: 73
atgagttcgc ttggggttacc gtacact                                             27

<210> SEQ ID NO 74
<211> LENGTH: 321
<212> TYPE: DNA
<213> ORGANISM: Artificial sequence
<220> FEATURE:
<223> OTHER INFORMATION: Synthetic 8B4-74C VL nucleic acid
```

<400> SEQUENCE: 74

```
gaaattgtgc tgactcagtc tccagacttt cagtctgtga ctccaaagga gaaagtcacc      60
atcacctgcc gggccagtca gagcattggt agtagcttac actggtacca gcagaaacca    120
gatcagtctc caaaactcct catcaagtat gcttcccagt ccttctcagg ggtcccctcg    180
aggttcagtg gcagtggatc tgggacagat ttcaccctca ccatcaatag cctggaagct    240
gaagatgctg cagcgtatta ctgtatgagt tcgcttgggt taccgtacac ttttggccag    300
gggaccaagc tggagatcaa a                                              321
```

<210> SEQ ID NO 75
<211> LENGTH: 336
<212> TYPE: PRT
<213> ORGANISM: Artificial sequence
<220> FEATURE:
<223> OTHER INFORMATION: Synthetic construct containing Fc domain of IgG1

<400> SEQUENCE: 75

```
Leu Val Thr Val Ser Ser Ala Ser Thr Lys Gly Pro Ser Val Phe Pro
1               5                   10                  15
Leu Ala Pro Ser Ser Lys Ser Thr Ser Gly Gly Thr Ala Ala Leu Gly
            20                  25                  30
Cys Leu Val Lys Asp Tyr Phe Pro Glu Pro Val Thr Val Ser Trp Asn
        35                  40                  45
Ser Gly Ala Leu Thr Ser Gly Val His Thr Phe Pro Ala Val Leu Gln
    50                  55                  60
Ser Ser Gly Leu Tyr Ser Leu Ser Ser Val Val Thr Val Pro Ser Ser
65                  70                  75                  80
Ser Leu Gly Thr Gln Thr Tyr Ile Cys Asn Val Asn His Lys Pro Ser
                85                  90                  95
Asn Thr Lys Val Asp Lys Lys Ala Glu Pro Lys Ser Cys Asp Lys Thr
            100                 105                 110
His Thr Cys Pro Pro Cys Pro Ala Pro Glu Leu Leu Gly Gly Pro Ser
        115                 120                 125
Val Phe Leu Phe Pro Pro Lys Pro Lys Asp Thr Leu Met Ile Ser Arg
    130                 135                 140
Thr Pro Glu Val Thr Cys Val Val Val Asp Val Ser His Glu Asp Pro
145                 150                 155                 160
Glu Val Lys Phe Asn Trp Tyr Val Asp Gly Val Glu Val His Asn Ala
                165                 170                 175
Lys Thr Lys Pro Arg Glu Glu Gln Tyr Asn Ser Thr Tyr Arg Val Val
            180                 185                 190
Ser Val Leu Thr Val Leu His Gln Asp Trp Leu Asn Gly Lys Glu Tyr
        195                 200                 205
Lys Cys Lys Val Ser Asn Lys Ala Leu Pro Ala Pro Ile Glu Lys Thr
    210                 215                 220
Ile Ser Lys Ala Lys Gly Gln Pro Arg Glu Pro Gln Val Tyr Thr Leu
225                 230                 235                 240
Pro Pro Ser Arg Asp Glu Leu Thr Lys Asn Gln Val Ser Leu Thr Cys
                245                 250                 255
Leu Val Lys Gly Phe Tyr Pro Ser Asp Ile Ala Val Glu Trp Glu Ser
            260                 265                 270
Asn Gly Gln Pro Glu Asn Asn Tyr Lys Thr Thr Pro Pro Val Leu Asp
        275                 280                 285
Ser Asp Gly Ser Phe Phe Leu Tyr Ser Lys Leu Thr Val Asp Lys Ser
```

```
            290                 295                 300
Arg Trp Gln Gln Gly Asn Val Phe Ser Cys Ser Val Met His Glu Ala
305                 310                 315                 320

Leu His Asn His Tyr Thr Gln Lys Ser Leu Ser Leu Ser Pro Gly Lys
                325                 330                 335

<210> SEQ ID NO 76
<211> LENGTH: 332
<212> TYPE: PRT
<213> ORGANISM: Artificial sequence
<220> FEATURE:
<223> OTHER INFORMATION: Synthetic construct containing Fc domain
      of IgG2

<400> SEQUENCE: 76

Leu Val Thr Val Ser Ser Ala Ser Thr Lys Gly Pro Ser Val Phe Pro
1               5                   10                  15

Leu Ala Pro Cys Ser Arg Ser Thr Ser Glu Ser Thr Ala Ala Leu Gly
                20                  25                  30

Cys Leu Val Lys Asp Tyr Phe Pro Glu Pro Val Thr Val Ser Trp Asn
            35                  40                  45

Ser Gly Ala Leu Thr Ser Gly Val His Thr Phe Pro Ala Val Leu Gln
    50                  55                  60

Ser Ser Gly Leu Tyr Ser Leu Ser Ser Val Val Thr Val Thr Ser Ser
65                  70                  75                  80

Asn Phe Gly Thr Gln Thr Tyr Thr Cys Asn Val Asp His Lys Pro Ser
                85                  90                  95

Asn Thr Lys Val Asp Lys Thr Val Glu Arg Lys Cys Cys Val Glu Cys
            100                 105                 110

Pro Pro Cys Pro Ala Pro Pro Val Ala Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Gln Phe
145                 150                 155                 160

Asn Trp Tyr Val Asp Gly Val Glu Val His Asn Ala Lys Thr Lys Pro
                165                 170                 175

Arg Glu Glu Gln Phe Asn Ser Thr Phe Arg Val Val Ser Val Leu Thr
            180                 185                 190

Val Val His Gln Asp Trp Leu Asn Gly Lys Glu Tyr Lys Cys Lys Val
        195                 200                 205

Ser Asn Lys Gly Leu Pro Ala Pro Ile Glu Lys Thr Ile Ser Lys Thr
210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Met Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330
```

<210> SEQ ID NO 77
<211> LENGTH: 333
<212> TYPE: PRT
<213> ORGANISM: Artificial sequence
<220> FEATURE:
<223> OTHER INFORMATION: Synthetic construct containing Fc domain of IgG4

<400> SEQUENCE: 77

```
Leu Val Thr Val Ser Ser Ala Ser Thr Lys Gly Pro Ser Val Phe Pro
1               5                   10                  15

Leu Ala Pro Cys Ser Arg Ser Thr Ser Glu Ser Thr Ala Ala Leu Gly
            20                  25                  30

Cys Leu Val Lys Asp Tyr Phe Pro Glu Pro Val Thr Val Ser Trp Asn
        35                  40                  45

Ser Gly Ala Leu Thr Ser Gly Val His Thr Phe Pro Ala Val Leu Gln
    50                  55                  60

Ser Ser Gly Leu Tyr Ser Leu Ser Ser Val Val Thr Val Pro Ser Ser
65                  70                  75                  80

Ser Leu Gly Thr Lys Thr Tyr Thr Cys Asn Val Asp His Lys Pro Ser
                85                  90                  95

Asn Thr Lys Val Asp Lys Arg Val Glu Ser Lys Tyr Gly Pro Pro Cys
            100                 105                 110

Pro Ser Cys Pro Ala Pro Glu Phe Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser Gln Glu Asp Pro Glu Val Gln
145                 150                 155                 160

Phe Asn Trp Tyr Val Asp Gly Val Glu Val His Asn Ala Lys Thr Lys
                165                 170                 175

Pro Arg Glu Glu Gln Phe Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Gly Leu Pro Ser Ser Ile Glu Lys Thr Ile Ser Lys
    210                 215                 220

Ala Lys Gly Gln Pro Arg Glu Pro Gln Val Tyr Thr Leu Pro Pro Ser
225                 230                 235                 240

Gln Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Arg Leu Thr Val Asp Lys Ser Arg Trp Gln
    290                 295                 300

Glu Gly Asn Val Phe Ser Cys Ser Val Met His Glu Ala Leu His Asn
305                 310                 315                 320

His Tyr Thr Gln Lys Ser Leu Ser Leu Gly Lys
                325                 330
```

<210> SEQ ID NO 78
<211> LENGTH: 332
<212> TYPE: PRT

<210> SEQ ID NO 78
<211> LENGTH: 330
<212> TYPE: PRT
<213> ORGANISM: Artificial sequence
<220> FEATURE:
<223> OTHER INFORMATION: Synthetic construct containing Fc domain of IgG2m4

<400> SEQUENCE: 78

```
Leu Val Thr Val Ser Ser Ala Ser Thr Lys Gly Pro Ser Val Phe Pro
  1               5                  10                  15
Leu Ala Pro Cys Ser Arg Ser Thr Ser Glu Ser Thr Ala Ala Leu Gly
             20                  25                  30
Cys Leu Val Lys Asp Tyr Phe Pro Glu Pro Val Thr Val Ser Trp Asn
         35                  40                  45
Ser Gly Ala Leu Thr Ser Gly Val His Thr Phe Pro Ala Val Leu Gln
     50                  55                  60
Ser Ser Gly Leu Tyr Ser Leu Ser Ser Val Val Thr Val Thr Ser Ser
 65                  70                  75                  80
Asn Phe Gly Thr Gln Thr Tyr Thr Cys Asn Val Asp His Lys Pro Ser
                 85                  90                  95
Asn Thr Lys Val Asp Lys Thr Val Glu Arg Lys Cys Cys Val Glu Cys
            100                 105                 110
Pro Pro Cys Pro Ala Pro Pro Val Ala Gly Pro Ser Val Phe Leu Phe
        115                 120                 125
Pro Pro Lys Pro Lys Asp Thr Leu Met Ile Ser Arg Thr Pro Glu Val
    130                 135                 140
Thr Cys Val Val Val Asp Val Ser Gln Glu Asp Pro Glu Val Gln Phe
145                 150                 155                 160
Asn Trp Tyr Val Asp Gly Val Glu Val His Asn Ala Lys Thr Lys Pro
                165                 170                 175
Arg Glu Glu Gln Phe Asn Ser Thr Phe Arg Val Val Ser Val Leu Thr
            180                 185                 190
Val Leu His Gln Asp Trp Leu Asn Gly Lys Glu Tyr Lys Cys Lys Val
        195                 200                 205
Ser Asn Lys Gly Leu Pro Ser Ser Ile Glu Lys Thr Ile Ser Lys Thr
    210                 215                 220
Lys Gly Gln Pro Arg Glu Pro Gln Val Tyr Thr Leu Pro Pro Ser Arg
225                 230                 235                 240
Glu Glu Met Thr Lys Asn Gln Val Ser Leu Thr Cys Leu Val Lys Gly
                245                 250                 255
Phe Tyr Pro Ser Asp Ile Ala Val Glu Trp Glu Ser Asn Gly Gln Pro
            260                 265                 270
Glu Asn Asn Tyr Lys Thr Thr Pro Pro Met Leu Asp Ser Asp Gly Ser
        275                 280                 285
Phe Phe Leu Tyr Ser Lys Leu Thr Val Asp Lys Ser Arg Trp Gln Gln
    290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly Lys
                325                 330
```

<210> SEQ ID NO 79
<211> LENGTH: 326
<212> TYPE: PRT
<213> ORGANISM: Artificial sequence
<220> FEATURE:
<223> OTHER INFORMATION: Synthetic Fc domain of IgG2m4

<400> SEQUENCE: 79

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325
```

<210> SEQ ID NO 80
<211> LENGTH: 978
<212> TYPE: DNA
<213> ORGANISM: Artificial sequence
<220> FEATURE:
<223> OTHER INFORMATION: Synthetic Fc domain of IgG2m4 nucleic acid

<400> SEQUENCE: 80

```
gcctccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgacctcca gcaactttgg cacgcagacc     240
```

```
tacacctgca acgtagatca caagcccagc aacaccaagg tggacaagac agttgagcgg    300
aaatgctgcg tggagtgccc accatgccca gcacctccag tggccggacc atcagtcttc    360
ctgttccccc caaaacccaa ggacactctc atgatctccc ggaccctga ggtcacgtgc     420 gtggtggtgg acgtgagcca ggaagacccc gaggtccagt tcaactggta cgtggatggc    480
gtggaggtgc ataatgccaa gacaaagccg cgggaggagc agttcaacag cacgttccgt    540
gtggtcagcg tcctcaccgt cctgcaccag gactggctga acggcaagga gtacaagtgc    600
aaggtctcca acaaaggcct cccgtcctcc atcgagaaaa ccatctccaa aaccaaaggg    660
cagccccgag agccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacgc ctcccatgct ggactccgac    840
ggctccttct cctctacag caagctaacc gtggacaaga gcaggtggca gcaggggaat    900
gtcttctcat gctccgtgat gcatgaggct ctgcacaacc actacacaca gaagagcctc    960
tccctgtctc ctggtaaa                                                  978
```

```
<210> SEQ ID NO 81
<211> LENGTH: 401
<212> TYPE: PRT
<213> ORGANISM: Homo sapiens

<400> SEQUENCE: 81
```

```
Ala Pro Thr Glu Thr Gln Pro Pro Val Thr Asn Leu Ser Val Ser Val
1               5                   10                  15

Glu Asn Leu Cys Thr Val Ile Trp Thr Trp Asn Pro Pro Glu Gly Ala
            20                  25                  30

Ser Ser Asn Cys Ser Leu Trp Tyr Phe Ser His Phe Gly Asp Lys Gln
        35                  40                  45

Asp Lys Lys Ile Ala Pro Glu Thr Arg Arg Ser Ile Glu Val Pro Leu
    50                  55                  60

Asn Glu Arg Ile Cys Leu Gln Val Gly Ser Gln Cys Ser Thr Asn Glu
65                  70                  75                  80

Ser Glu Lys Pro Ser Ile Leu Val Glu Lys Cys Ile Ser Pro Pro Glu
                85                  90                  95

Gly Asp Pro Glu Ser Ala Val Thr Glu Leu Gln Cys Ile Trp His Asn
            100                 105                 110

Leu Ser Tyr Met Lys Cys Ser Trp Leu Pro Gly Arg Asn Thr Ser Pro
        115                 120                 125

Asp Thr Asn Tyr Thr Leu Tyr Tyr Trp His Arg Ser Leu Glu Lys Ile
    130                 135                 140

His Gln Cys Glu Asn Ile Phe Arg Glu Gly Gln Tyr Phe Gly Cys Ser
145                 150                 155                 160

Phe Asp Leu Thr Lys Val Lys Asp Ser Ser Phe Glu Gln His Ser Val
                165                 170                 175

Gln Ile Met Val Lys Asp Asn Ala Gly Lys Ile Lys Pro Ser Phe Asn
            180                 185                 190

Ile Val Pro Leu Thr Ser Arg Val Lys Pro Asp Pro Pro His Ile Lys
        195                 200                 205

Asn Leu Ser Phe His Asn Asp Asp Leu Tyr Val Gln Trp Glu Asn Pro
    210                 215                 220

Gln Asn Phe Ile Ser Arg Cys Leu Phe Tyr Glu Val Glu Val Asn Asn
225                 230                 235                 240
```

```
Ser Gln Thr Glu Thr His Asn Val Phe Tyr Val Gln Glu Ala Lys Cys
                245                 250                 255

Glu Asn Pro Glu Phe Glu Arg Asn Val Glu Asn Thr Ser Cys Phe Met
            260                 265                 270

Val Pro Gly Val Leu Pro Asp Thr Leu Asn Thr Val Arg Ile Arg Val
        275                 280                 285

Lys Thr Asn Lys Leu Cys Tyr Glu Asp Lys Leu Trp Ser Asn Trp
    290                 295                 300

Ser Gln Glu Met Ser Ile Gly Lys Lys Arg Asn Ser Thr Leu Tyr Ile
305                 310                 315                 320

Thr Met Leu Leu Ile Val Pro Val Ile Val Ala Gly Ala Ile Ile Val
                325                 330                 335

Leu Leu Leu Tyr Leu Lys Arg Leu Lys Ile Ile Ile Phe Pro Pro Ile
                340                 345                 350

Pro Asp Pro Gly Lys Ile Phe Lys Glu Met Phe Gly Asp Gln Asn Asp
            355                 360                 365

Asp Thr Leu His Trp Lys Lys Tyr Asp Ile Tyr Glu Lys Gln Thr Lys
            370                 375                 380

Glu Glu Thr Asp Ser Val Val Leu Ile Glu Asn Leu Lys Lys Ala Ser
385                 390                 395                 400

Gln

<210> SEQ ID NO 82
<211> LENGTH: 324
<212> TYPE: PRT
<213> ORGANISM: Homo sapiens

<400> SEQUENCE: 82

Asp Tyr Lys Asp Asp Asp Glu Ser Arg Thr Glu Thr Gln Pro Pro Val
1               5                   10                  15

Thr Asn Leu Ser Val Ser Val Glu Asn Leu Cys Thr Val Ile Trp Thr
                20                  25                  30

Trp Asn Pro Pro Glu Gly Ala Ser Ser Asn Cys Ser Leu Trp Tyr Phe
            35                  40                  45

Ser His Phe Gly Asp Lys Gln Asp Lys Lys Ile Ala Pro Glu Thr Arg
    50                  55                  60

Arg Ser Ile Glu Val Pro Leu Asn Glu Arg Ile Cys Leu Gln Val Gly
65                  70                  75                  80

Ser Gln Cys Ser Thr Asn Glu Ser Glu Lys Pro Ser Ile Leu Val Glu
                85                  90                  95

Lys Cys Ile Ser Pro Pro Glu Gly Asp Pro Glu Ser Ala Val Thr Glu
            100                 105                 110

Leu Gln Cys Ile Trp His Asn Leu Ser Tyr Met Lys Cys Ser Trp Leu
        115                 120                 125

Pro Gly Arg Asn Thr Ser Pro Asp Thr Asn Tyr Thr Leu Tyr Tyr Trp
    130                 135                 140

His Arg Ser Leu Glu Lys Ile His Gln Cys Glu Asn Ile Phe Arg Glu
145                 150                 155                 160

Gly Gln Tyr Phe Gly Cys Ser Phe Asp Leu Thr Lys Val Lys Asp Ser
                165                 170                 175

Ser Phe Glu Gln His Ser Val Gln Ile Met Val Lys Asp Asn Ala Gly
            180                 185                 190

Lys Ile Lys Pro Ser Phe Asn Ile Val Pro Leu Thr Ser Arg Val Lys
        195                 200                 205

Pro Asp Pro Pro His Ile Lys Asn Leu Ser Phe His Asn Asp Asp Leu
```

```
                        210                 215                 220
Tyr Val Gln Trp Glu Asn Pro Gln Asn Phe Ile Ser Arg Cys Leu Phe
225                 230                 235                 240

Tyr Glu Val Glu Val Asn Asn Ser Gln Thr Glu Thr His Asn Val Phe
                245                 250                 255

Tyr Val Gln Glu Ala Lys Cys Glu Asn Pro Glu Phe Glu Arg Asn Val
                260                 265                 270

Glu Asn Thr Ser Cys Phe Met Val Pro Gly Val Leu Pro Asp Thr Leu
                275                 280                 285

Asn Thr Val Arg Ile Arg Val Lys Thr Asn Lys Leu Cys Tyr Glu Asp
                290                 295                 300

Asp Lys Leu Trp Ser Asn Trp Ser Gln Glu Met Ser Ile Gly Lys Lys
305                 310                 315                 320

Arg Asn Ser Thr

<210> SEQ ID NO 83
<211> LENGTH: 57
<212> TYPE: DNA
<213> ORGANISM: Artificial sequence
<220> FEATURE:
<223> OTHER INFORMATION: Synthetic 4A10 VH CDR3

<400> SEQUENCE: 83
gagattacta taatgcgggg acttattaaa aactactact attatggtat ggacgtc        57

<210> SEQ ID NO 84
<211> LENGTH: 27
<212> TYPE: DNA
<213> ORGANISM: Artificial sequence
<220> FEATURE:
<223> OTHER INFORMATION: Synthetic 6C11 VH CDR3

<400> SEQUENCE: 84
ggggaagggc actggttctt cgatgtc                                          27

- 35 -
```

ANTIBODY ANTAGONISTS OF INTERLEUKIN-13 RECEPTOR α1

INTRODUCTION

This application claims benefit of PCT/US2007/081889, filed Oct. 19, 2007, which claims benefit of U.S. provisional patent application Ser. No. 60/852,748 filed Oct. 19, 2006, the contents of which are incorporated herein by reference in their entireties.

BACKGROUND OF THE INVENTION

Data from human studies and experimental animal models strongly implicate Th2-derived cytokines as contributing to atopic asthma, with interleukin-4 (IL-4) and interleukin-13 (IL-13; see, e.g., Minty et al., 1993 *Nature* 362:248-250; McKenzie et al., 1993 *Proc. Natl. Acad. Sci. USA* 90:3735-3739; Accession Nos: U31120 and L13029 (human) and NM_001032929 (*Macaca mulatta*)) playing the most central role. These two cytokines have significant structural similarities and share certain receptor components. The receptor that IL-4 and IL-13 share is a dual IL-4R/IL-13 receptor (or type II receptor) which binds both IL-4 and IL-13. This receptor is composed of the IL-4Rα chain (see, e.g., Idzerda et al., 1990 *J. Exp. Med.* 171:861-873) and the IL-13Rα1 chain (see, e.g., Hilton et al., 1996 *Proc. Natl. Acad. Sci. USA* 93:497-501; Aman et al., 1996 *J. Biol. Chem.* 271:29265-29270; Miloux et al., 1997 *FEBS Lett.* 401:163-166; Accession Nos: U62858 and CAA70508 (human) and AAP78901 (*Macaca fascicularis*)). The dual IL-4R/IL-13R receptor is expressed on hematopoietic and non-hematopoietic cells, including lung epithelial and smooth muscle cells. Both IL-4 and IL-13, additionally, each have one receptor that recognizes them to the exclusion of the other. For instance, IL-4 receptor (IL-4R) type I, composed of the IL-4Rα chain and the common gamma chain ("γc"), specifically binds IL-4. IL-4R type I is expressed exclusively on cells of hematopoietic origin. The receptor specific for IL-13, IL-13Rα2, binds IL-13 with high affinity, but apparently does not transduce signals. Rather, the receptor acts as a decoy to attenuate the response to IL-13.

IL-13 and IL-4 carry out a number of functions and both regulate a number of functions related to the allergic phenotype, such as isotype class switching to IgE in B-cells, activation of mast cells and eosinophils, up-regulation of vascular cell adhesion molecule-1 (VCAM-1) on endothelial cells, and production of chemokines such as eotaxins, thymus and activation-regulated chemokine (TARC), and macrophage-derived chemokine (MDC).

IL-4 and IL-13, though, have many distinct functions in vitro and in vivo owing to differences in their receptor complexes. For instance, sequestration of IL-13, but not IL-4, has been shown to prevent airway hyperreactivity and reduce mucous production in mouse asthma models. This correlation between IL-13 and the asthmatic response has been further supported by other studies; see, e.g., Hershey et al., 2003 *J. Allergy Clin. Immunol.* 111(4):677-690; Grunig et al., 1998 *Science* 282(5397):2261-2263; Mattes et al., 2001 *J. Immunol.* 167(3):1683-1692; and Fulkerson et al., 2006 *Am. J. Respir. Cell. Mol. Biol.* 35(3)337-346. Delivery of IL-13 to the lung, for example, has been found to be sufficient to induce the entire asthma-like phenotype in mice. Treated animals develop airway hyperreactivity, eosinophil-rich cell inflammation, goblet cell hyperplasia with associated mucous overproduction, and subepithelial fibrosis; see, e.g., Wills-Karp et al., 1998 *Science* 282(5397): 2258-2261; Reiman et al., 2006 *Infect. Immun.* 74(3): 1471-1479; and Kaviratne et al., 2004 *J. Immunol.* 173(6):4020-4029. Expression of IL-13 has, furthermore, been reported to be elevated in the lungs of human asthmatics. In addition, several groups have reported associations of polymorphisms in the IL-13 gene with an increased risk of allergic traits and asthma symptoms. Some of these polymorphisms have been shown to be correlated with increased expression of IL-13; see, e.g., Huang et al., 1995 *J. Immunol.* 155(5)2688-2694; Naseer et al., 1997 *Am. J. Respir. Crit. Care Med.* 155(3):845-851; Vladich et al., 2005 *J. Clin. Invest.* 115(3):747-754; Chen et al., 2004 *J. Allergy Clin. Immunol.* 114(3):553-560; and Vercelli et al., 2002 *Curr. Opin. Allergy Clin. Immunol.* 2(5):389-393.

IL-13 has also been associated with various other conditions, including but not limited to, various respiratory and allergy-mediated disorders, fibrosis, scleroderma, inflammatory bowel disease and certain cancers; see, e.g., Wynn, T. A., 2003 *Annu. Rev. Immunol.* 21:425-456; Terabe et al., 2000 *Nat. Immunol.* 1(6):515-520; Fuss et al., 2004 *J. Clin. Invest.* 113(10):1490-1497; Simms et al., 2002 *Curr. Opin. Rheumatol.* 14(6):717-722; and Hasegawa et al., 1997 *J. Rheumatol.* 24(2):328-332.

An antagonist of IL-13 would, therefore, be a highly attractive molecule for use in the development of a treatment for IL-13-associated disorders. An effective antibody antagonist would interfere with the binding of IL-13 to IL-13R. An effective antibody antagonist to IL-13Rα1 may also interfere with the binding of IL-13 and prevent heterodimerization of IL-4Rα and IL-13Rα1. Such an antibody could inhibit signaling of both IL-13 and IL-4 through the type II receptor while sparing IL-4 signaling through the type I receptor. Signaling through the type I receptor is essential in the induction phase of the immune response during which Th2 cells differentiate. T cells do not express IL-13Rα1 so the type II receptor plays no role in Th2 differentiation. Hence, an IL-13Rα1 antibody should not affect the overall Th1/Th2 balance. Signaling through the type II IL-4/IL-13 receptor is critical during the effector stage of the immune response during established allergic inflammation. Thus, blockade of the type II receptor should have a beneficial effect on many of the symptoms of asthma and other IL-13R-mediated conditions and should, therefore, be an effective disease modifying agent.

Antibodies against IL-13Rα1 (both monoclonal and polyclonal) have been described in the art; see, e.g., WO 97/15663, WO 03/80675; WO 03/46009; WO 06/072564; Gauchat et al., 1998 *Eur. J. Immunol.* 28:4286-4298; Gauchat et al., 2000 *Eur. J. Immunol.* 30:3157-3164; Clement et al., 1997 *Cytokine* 9(11):959 (Meeting Abstract); Ogata et al., 1998 *J. Biol. Chem.* 273:9864-9871; Graber et al., 1998 *Eur. J. Immunol.* 28:4286-4298; C. Vermot-Desroches et al., 2000 *Tissue Antigens* 5(Supp. 1):52-53 (Meeting Abstract); Poudrier et al., 2000 *Eur. J. Immunol.* 30:3157-3164; Akaiwa et al., 2001 *Cytokine* 13:75-84; Cancino-Diaz et al., 2002 *J. Invest. Dermatol.* 119:1114-1120; and Krause et al., 2006 *Mol. Immunol.* 43:1799-1807.

There is a need for an antibody with effective biological activity that could impact activities associated with the allergy and asthmatic response as well as other various conditions that have been attributed at least in part to an increased expression/functioning of IL-13Rα1. There is further a need for an antibody molecule with affinity for IL-13Rα1 with low immunogenicity in humans. Accordingly, it would be of great import to produce a therapeutic-based human antibody antagonist of IL-13Rα1 that inhibits or antagonizes the activity of IL-13Rα1 and the corresponding role IL-13Rα1 plays in various therapeutic conditions.

SUMMARY OF THE INVENTION

The present invention relates to antibody antagonists of IL-13Rα1 and particularly human IL-13Rα1. Disclosed antibody molecules selectively recognize IL-13Rα1, particularly human IL-13Rα1, exhibiting binding to human IL-13Rα1 with a $K_D$ of less than 20 nM, preferably less than 10 nM and, more preferably, less than 5 nM, as determined by surface plasmon resonance assay against chip bound extracellular domain of hIL-13Rα1, e.g., BIACORE™ (Upsala, Sweden) or suitable equivalent thereof. Antibody molecules in accordance herewith are effective in the inhibition of IL-13Rα1-mediated activities and, thus, are of import in the treatment of conditions associated therewith, including, but not limited to, asthma, allergy, allergic rhinitis, chronic sinusitis, hay fever, atopic dermatitis, chronic obstructive pulmonary disease (COPD), pulmonary fibrosis, esophageal eosinophilia, scleroderma, psoriasis, psoriatic arthritis, fibrosis, inflammatory bowel disease (particularly, ulcerative colitis), anaphylaxis, and cancer (particularly, Hodgkin's lymphoma, glioma, and renal carcinoma), and general Th2-mediated disorders/conditions. IL-13Rα1-specific antibodies also have utility for various diagnostic purposes in the detection and quantification of IL-13Rα1.

The present invention provides, in one particular aspect, isolated antibodies 2B6, 4A10, 6C11, and 8B4 which antagonize IL-13, functioning through IL-13Rα1. Said antibodies have proven effective in inhibiting IL-13-induced eotaxin release in NHDF cells. 2B6, 6C11 and 8B4 were additionally tested and proven effective as follows: 2B6, 6C11 and 8B4 for inhibition of IL-13-induced STAT6 phosphorylation, and 8B4 for inhibition of IL-13-induced TARC release in whole blood or peripheral blood mononuclear cells (PBMCs). The present invention, thus, encompasses antibodies as produced by the hybridoma cell lines deposited as ATCC Deposit Nos. PTA-6932 (2B6), PTA-6930 (6C11), and PTA-6934 (8B4). Moreover, the present invention encompasses an isolated antibody, wherein (a) the heavy chain variable region of said antibody includes CDR1, CDR2 and CDR3 amino acid sequences as set forth in (i) SEQ ID NOs:2, 3 and 4, respectively; (ii) SEQ ID NOs:14, 15 and 16, respectively; (iii) or SEQ ID NOs:22, 15 and 23, respectively; and (b) the light chain variable region of said antibody includes CDR1, CDR2 and CDR3 sequences as set forth in (i) SEQ ID NOs:6, 7 and 8, respectively; or (ii) SEQ ID NOs: 18, 19 and 20, respectively. In particular embodiments, an antibody of the invention includes (a) a heavy chain variable region having an amino acid sequence as set forth in SEQ ID NO:1, SEQ ID NO:9, SEQ ID NO:13, or SEQ ID NO:21; or a sequence at least 90% homologous thereto; (b) a light chain variable region having an amino acid sequence as set forth in SEQ ID NO:5 or SEQ ID NO:17; or a sequence at least 90% homologous thereto; or (c) a combination of (a) and (b).

The present invention also encompasses antibodies that compete for binding to hIL-13Rα1 with an antibody of ATCC Deposit Nos. PTA-6932 (2B6), PTA-6930 (6C11), and PTA-6934 (8B4); or an antibody described herein as 4A10. Particular embodiments of the present invention include antibody molecules comprising heavy and/or light chain variable region sequences of 2B6, 4A10, 6C11, and 8B4, as well as equivalents (characterized as having one or more conservative amino acid substitutions) or homologs thereof.

Particular embodiments include isolated antibody molecules that have the CDR domains disclosed herein or sets of heavy and/or light chain CDR domains disclosed herein, or equivalents thereof, characterized as having one or more conservative amino acid substitutions.

As will be appreciated by those skilled in the art, fragments of an antibody that retain the ability to bind to hIL-13Rα1 may be inserted into various frameworks, see, e.g., U.S. Pat. No. 6,818,418 and references contained therein which discuss various scaffolds which may be used to display antibody loops previously selected on the basis of antigen binding. In addition, genes encoding for $V_L$ and $V_H$ can be joined, using recombinant methods, for example using a synthetic linker that enables them to be made as a single protein chain in which the $V_L$ and $V_H$ regions pair to form monovalent molecules, otherwise known as single chain Fvs (ScFVs); see, e.g., Bird et al., 1988 *Science* 242: 423-426, and Huston et al., 1988 *Proc. Natl. Acad. Sci. USA* 85:5879-5883.

In another aspect, the present invention provides nucleic acid encoding the disclosed antibody molecules. The present invention also provides nucleic acid encoding the variable heavy and light chains and select components thereof, particularly the disclosed respective CDR3 regions.

In another aspect, the present invention provides vectors including said nucleic acid. In another aspect, the present invention provides isolated cell(s) harboring nucleic acid encoding the disclosed antibody molecules and components thereof as described. In another aspect, the present invention provides isolated cell(s) comprising a polypeptide, or vector of the present invention.

In another aspect, the present invention provides a method of making an antibody molecule which selectively binds IL-13Rα1 (inclusive of antibodies, antigen binding fragments, derivatives, chimeric molecules, fusions of any of the foregoing with another polypeptide, or alternative structures/compositions incorporating any of the foregoing) of the present invention, which involves incubating a cell harboring a nucleic acid encoding a heavy and/or a light chain (depending on the antibody molecule being produced) under conditions that allow for the expression and/or assembly of said heavy and/or light chains into the antibody molecule, and isolating said antibody molecule from the cell. One of skill in the art can obtain the antibody molecules disclosed herein as well using standard recombinant DNA techniques.

In another aspect, the present invention provides a method for antagonizing the activity or function of IL-13Rα1, be it signaling or other, which involves contacting a cell expressing IL-13Rα1 with an antibody molecule disclosed herein under conditions that allow said antibody molecule to bind to IL-13Rα1. Specific embodiments of the present invention include such methods wherein the cell is a human cell. Antibody molecules in accordance herewith are effective in the inhibition of IL-13Rα1-mediated activities. Antibody molecules in accordance with the present invention were found to effectively inhibit eotaxin release from normal human dermal fibroblast cells (hereinafter, NHDF cells), effectively inhibit IL-13-stimulated STAT6 phosphorylation in NHDF cells, and/or to effectively inhibit the IL-13-stimulated release of TARC(CCL17) in whole blood (human/rhesus).

In another aspect, the present invention provides a method of antagonizing the activity of IL-13Rα1 in a subject exhibiting a condition associated with IL-13Rα1 activity (or a condition where the functioning of IL-13Rα1 is deemed not beneficial to the particular subject), which involves administering to the subject a therapeutically effective amount of an antibody molecule of the present invention. In select embodiments, the condition may be asthma, allergy, allergic rhinitis, chronic sinusitis, hay fever, atopic dermatitis, chronic obstructive pulmonary disease (COPD), pulmonary fibrosis, esophageal eosinophilia, psoriasis, psoriatic arthritis, fibrosis, scleroderma, inflammatory bowel disease (particularly, ulcerative colitis), anaphylaxis, and cancer (particularly, Hodgkin's lymphoma, glioma, and renal carcinoma), and general Th2-mediated disorders/conditions. In another aspect, the present invention provides a pharmaceutical composition or other composition including an antibody molecule of the invention (or alternative antigen-binding structure or protein that has an IL-13Rα1-specific antigen binding portion disclosed herein) and a pharmaceutically acceptable carrier, excipient, diluent, stabilizer, buffer, or alternative designed to facilitate administration of the antibody molecule in the desired amount to the treated individual.

BRIEF DESCRIPTION OF THE DRAWINGS

FIG. 2 illustrates a sequence comparison of the Fc domains of IgG1 (SEQ ID NO:75), IgG2 (SEQ ID NO:76), IgG4 (SEQ ID NO:77) and the IgG2 m4 (SEQ ID NO:78) isotypes.

DETAILED DESCRIPTION OF THE INVENTION

Figure 1:
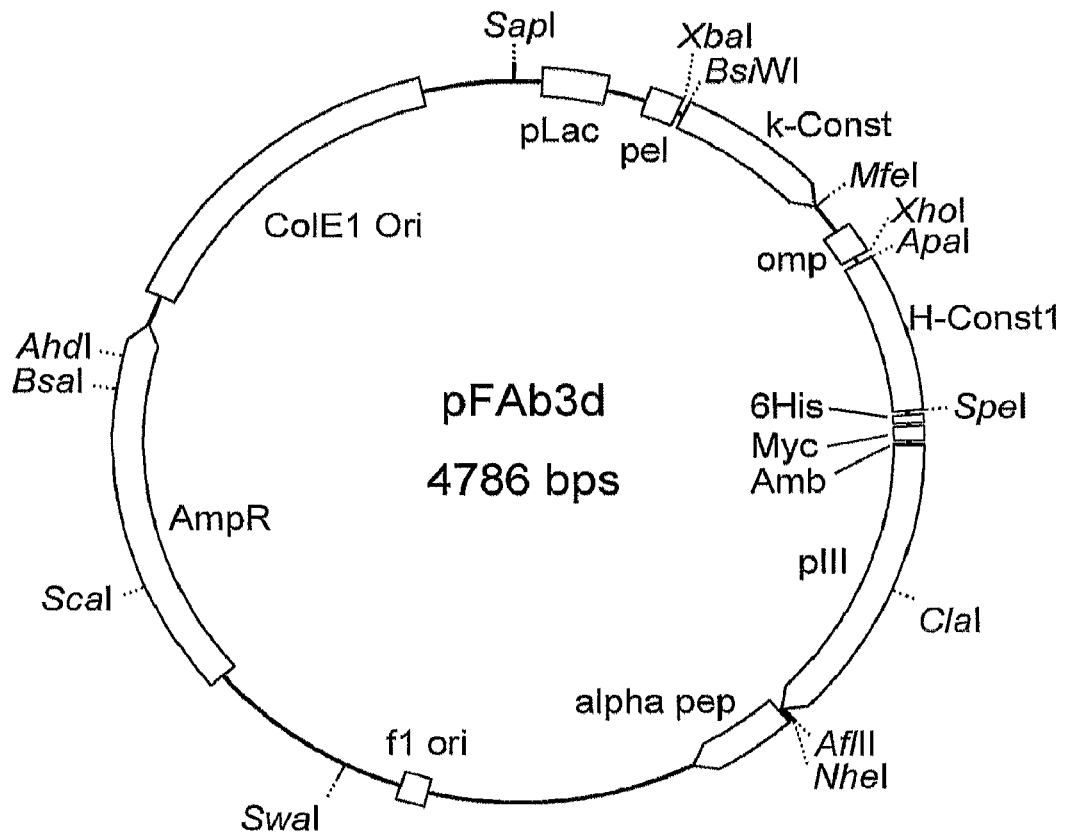
FIG. 1 illustrates a genetic map of pFab3d.

The present invention relates to antibody antagonists of IL-13Rα1 and particularly human IL-13Rα1. Disclosed antibody molecules selectively recognize and specifically bind to IL-13Rα1. Use of the terms "selective" or "specific" refers to the fact that the disclosed antibody molecules do not show significant binding to other than IL-13Rα1. The disclosed antibody molecules bind to human IL-13Rα1 with a $K_D$ of less than 20 nM, preferably less than 10 nM and, more preferably, less than 5 nM, as determined by surface plasmon resonance assay against chip bound extracellular domain of hIL-13Rα1, e.g., BIACORE™ (PHARMACIA AB Corporation, Upsala, Sweden) or suitable equivalent thereof. $K_D$ refers to the dissociation constant obtained from the ratio of $K_d$ (the dissociation rate of a particular antibody-antigen interaction) to $K_a$ (the association rate of the particular antibody-antigen interaction), or $K_d/K_a$ which is expressed as a molar concentration (M). $K_D$ values can be determined using methods well-established in the art. A preferred method for determining the $K_D$ of an antibody is by using surface plasmon resonance, for example a biosensor system such as a BIACORE™ (PHARMACIA AB Corporation) system.

Antibodies as described herein are effective in antagonizing IL-13Rα1 function, or IL-13Rα1-mediated activity as referred to herein. The language "IL-13Rα1-mediated" activity/function is used herein to refer to any activity/function that requires, or is exacerbated or enhanced by, the function of IL-13Rα1. The disclosed antibody molecules have been shown to exhibit at least one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCs. Specific embodiments of the present invention provide antibody molecules that antagonize IL-13Rα1-mediated eotaxin release from NHDF cells with an $IC_{50}$ of 20 nM or less, more preferably, 10 nM or less, and more preferably yet, 5 nM or less. Specific embodiments of the present invention provide antibody molecules that antagonize IL-13Rα1-mediated STAT6 phosphorylation in NHDF cells. Specific embodiments of the present invention provide antibody molecules that antagonize IL-13Rα1-mediated TARC (CCL17) release in whole blood or PBMCs. The extent of antagonism by any particular antibody may be measured quantitatively as the $IC_{50}$ value in statistical comparison to a control, or via any alternative method available in the art for assessing a negative effect on, or inhibition of, IL-13Rα1 function (i.e., any method capable of assessing antagonism of IL-13Rα1 function).

"Antibody molecule" or "antibody" as described herein refers to an immunoglobulin-derived structure with selective binding to hIL-13Rα1 including, but not limited to, a full-length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which incorporates any of the foregoing for purposes of selectively binding/inhibiting the function of IL-13Rα1. "Whole" antibodies or "full-length" antibodies refer to proteins that have two heavy (H) and two light (L) chains inter-connected by disulfide bonds which include: (1) in terms of the heavy chains, a variable region (abbreviated herein as "$V_H$") and a heavy chain constant region which has three domains, $C_{H1}$, $C_{H2}$ and $C_{H3}$; and (2) in terms of the light chains, a light chain variable region (abbreviated herein as "$V_L$") and a light chain constant region which comprises one domain, $C_L$. "Isolated" as used herein describes a property as it pertains to the disclosed antibody molecules, nucleic acid or other that makes them different from that found in nature. The difference can be, for example, that they are of a different purity than that found in nature, or that they are of a different structure or form part of a different structure than that found in nature. A structure not found in nature, for example, includes recombinant human immunoglobulin structures including, but not limited to, recombinant human immunoglobulin structures with optimized CDRs. Other examples of structures not found in nature are antibody molecules or nucleic acid substantially free of other cellular material. Isolated antibodies are generally free of other antibodies having different antigenic specificities (other than IL-13Rα1).

Antibody fragments and, more specifically, antigen binding fragments are molecules possessing an antibody variable region or segment thereof (which comprises one or more of the disclosed CDR 3 domains, heavy and/or light), which confers selective binding to IL-13Rα1, and particularly human IL-13Rα1 (hIL-13Rα1). Antibody fragments containing such an antibody variable region include, but are not limited to the following antibody molecules: a Fab, a F(ab')$_2$, a Fd, a Fv, a scFv, bispecific antibody molecules (antibody molecules including an IL-13Rα1-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, an isolated CDR3, a minibody, a 'scAb', a dAb fragment, a diabody, a triabody, a tetrabody, and artificial antibodies based upon protein scaffolds, including but not limited to fibronectin type III polypeptide antibodies (see, e.g., U.S. Pat. No. 6,703,199 and WO 02/32925 and WO 00/34784) or cytochrome B; see, e.g., Nygren et al., 1997 Curr. Opinion Struct. Biol. 7:463-469. The antibody portions or binding fragments may be natural, or partly or wholly synthetically produced. Such antibody portions can be prepared by various means known by one of skill in the art, including, but not limited to, conventional techniques, such as papain or pepsin digestion.

The present invention provides, in one particular aspect, isolated antibodies 2B6, 4A10, 6C11, and 8B4 which effectively antagonize IL-13 functioning through IL-13Rα1. Said antibodies have proven effective in inhibiting IL-13-induced eotaxin release in NHDF cells. 2B6, 6C11 and 8B4 were additionally tested and proven effective as follows: 2B6, 6C11 and 8B4, for inhibition of IL-13-induced STAT6 phosphorylation; and 8B4 for inhibition of IL-13-induced TARC release in whole blood or peripheral blood mononuclear cells (PBMCs). The present invention, thus, encompasses antibodies as produced by the hybridoma cell lines deposited as ATCC Deposit Nos. PTA-6932 (2B6), PTA-6930 (6C11), and PTA-6934 (8B4). The present invention also encompasses antibodies that compete for binding to hIL-13Rα1 with an antibody of ATCC Deposit Nos. PTA-6932 (2B6), PTA-6930 (6C11), and PTA-6934 (8B4); or an antibody described herein as 4A10. Additional embodiments of the present invention are antibody molecules that compete for binding to hIL-13Rα1 with antibodies disclosed herein. Specific embodiments of the present invention provide isolated antibody molecules which inhibit the binding of IL-13 to hIL-13Rα1.

Particular embodiments of the present invention include antibody molecules including heavy and/or light chain variable region sequences of 2B6, 4A10, 6C11, or 8B4, as well as equivalents (characterized as having one or more conservative amino acid substitutions) or homologs thereof. Particular embodiments are isolated antibody molecules that include the CDR domains disclosed herein or sets of heavy and/or light chain CDR domains disclosed herein, or equivalents thereof, characterized as having one or more conservative amino acid substitutions. Use of the terms "domain" or "region" herein simply refers to the respective portion of the antibody molecule wherein the sequence or segment at issue will reside or, in the alternative, currently resides.

In specific embodiments, the present invention provides isolated antibody molecules including a heavy chain variable region with a sequence selected from the group consisting of: SEQ ID NO:1, SEQ ID NO:9, SEQ ID NO:13 and SEQ ID NO:21, equivalents thereof characterized as having one or more conservative amino acid substitutions, and homologs thereof. The disclosed antibodies exhibit at least one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCs. In specific embodiments, the present invention provides homologs of the disclosed antibody molecules characterized as being at least 90% homologous thereto and exhibiting at least one of the above functional properties. Specific antibodies provided will compete for binding to hIL-13Rα1 with an antibody as produced by the hybridoma cell lines deposited as ATCC Deposit Nos. PTA-6932 (2B6), PTA-6930 (6C11), or PTA-6934 (8B4); or an antibody described herein as 4A10.

Table 1 provides a generalized outline of the molecules particularly embraced by the present invention.

TABLE 1

| SEQ ID NO: | DESCRIPTION |
| --- | --- |
| 1 | 2B6 VH |
| 2 | 2B6 VH CDR1 |
| 3 | 2B6 VH CDR2 |
| 4 | 2B6 VH CDR3 |
| 5 | 2B6 VL |
| 6 | 2B6 VL CDR1 |
| 7 | 2B6 VL CDR2 |
| 8 | 2B6 VL CDR3 |
| 9 | 4A10 VH |
| 10 | 4A10 VH CDR1 |
| 11 | 4A10 VH CDR2 |
| 12 | 4A10 VH CDR3 |
| 13 | 6C11 VH |
| 14 | 6C11 VH CDR1 |
| 15 | 6C11/8B4 VH CDR2 |
| 16 | 6C11 VH CDR3 |
| 17 | 6C11/8B4 VL |
| 18 | 6C11/8B4 VL CDR1 |
| 19 | 6C11/8B4 VL CDR2 |
| 20 | 6C11/8B4 VL CDR3 |
| 21 | 8B4 VH |
| 22 | 8B4 VH CDR1 |
| 23 | 8B4 VH CDR3 |
| 24 | 8B4-78M VL CDR3 |
| 25 | 8B4-82 VL CDR3 |
| 26 | 8B4-18C VL CDR3 |
| 27 | 8B4-36 VL CDR3 |
| 28 | 8B4-21C VL CDR3 |
| 29 | 8B4-74C VL CDR3 |
| 30 | 2B6 VH nucleic acid |
| 31 | 2B6 VH CDR1 nucleic acid |
| 32 | 2B6 VH CDR2 nucleic acid |
| 33 | 2B6 VH CDR3 nucleic acid |
| 34 | 2B6 VL nucleic acid |
| 35 | 2B6 VL CDR1 nucleic acid |
| 36 | 2B6 VL CDR2 nucleic acid |
| 37 | 2B6 VL CDR3 nucleic acid |
| 38 | 4A10 VH nucleic acid |
| 39 | 4A10 VH CDR1 nucleic acid |
| 40 | 4A10 VH CDR2 nucleic acid |
| 41 | 4A10 VH CDR3 nucleic acid |
| 42 | 6C11 VH nucleic acid |
| 43 | 6C11 VH CDR1 nucleic acid |
| 44 | 6C11/8B4 VH CDR2 nucleic acid |
| 45 | 6C11 VH CDR3 nucleic acid |
| 46 | 6C11/8B4 VL nucleic acid |
| 47 | 6C11/8B4 VL CDR1 nucleic acid |
| 48 | 6C11/8B4 VL CDR2 nucleic acid |
| 49 | 6C11/8B4 VL CDR3 nucleic acid |
| 50 | 8B4 VH nucleic acid |
| 51 | 8B4 VH CDR1 nucleic acid |
| 52 | 8B4 VH CDR3 nucleic acid |
| 53 | 8B4-78M VL |
| 54 | 8B4-82 VL |
| 55 | 8B4-18C VL |
| 56 | 8B4-36 VL |
| 57 | 8B4-21C VL |
| 58 | 8B4-74C VL |
| 59 | 8B4 VL forward primer |
| 60 | 8B4 VL reverse primer |
| 61 | 8B4 VH forward primer |
| 62 | 8B4 VH reverse primer |
| 63 | 8B4-80C VL CDR3 |
| 64 | 8B4-80C VL |
| 65 | 8B4-78 M VL CDR3 nucleic acid |
| 66 | 8B4-78M VL nucleic acid |
| 67 | 8B4-82 VL CDR3 nucleic acid |
| 68 | 8B4-82 VL nucleic acid |
| 69 | 8B4-18C VL CDR3 nucleic acid |
| 70 | 8B4-18C VL nucleic acid |
| 71 | 8B4-36 VL CDR3 nucleic acid |
| 72 | 8B4-36 VL nucleic acid |
| 73 | 8B4-74C VL CDR3 nucleic acid |
| 74 | 8B4-74C VL nucleic acid |
| 75 | Contains Fc domain of IgG1 |
| 76 | Contains Fc domain of IgG2 |
| 77 | Contains Fc domain of IgG4 |
| 78 | Contains Fc domain of IgG2m4 |
| 79 | Fc domain of IgG2m4 |
| 80 | Fc domain of IgG2m4 nucleic acid |
| 81 | Mature human IL-13 receptor α1 |
| 82 | hIL-13Rα1.ECR |
| 83 | 4A10 VH CDR3 nucleic acid |
| 84 | 6C11 VH CDR3 nucleic acid |

In specific embodiments, the present invention provides isolated antibody molecules including a light chain variable region with a sequence selected from the group consisting of: SEQ ID NO:5 and SEQ ID NO:17, equivalents thereof characterized as having one or more conservative amino acid substitutions, and homologs thereof. The disclosed antibodies exhibit at least one of the following functional properties: (i) inhibition of IL-13-induced eotaxin release in NHDF cells;

(ii) inhibition of IL-13-induced STAT6 phosphorylation in NHDF cells; or (iii) inhibition of IL-13-stimulated release of TARC in blood or PBMCs. In specific embodiments, the present invention provides homologs of the disclosed antibody molecules characterized as being at least 90% homologous thereto and exhibiting at least one of the above functional properties. Specific antibodies provided will compete for binding to hIL-13Rα1 with an antibody as produced by the hybridoma cell lines deposited as ATCC Deposit Nos. PTA-6932 (2B6), PTA-6930 (6C11), or PTA-6934 (8B4); or an antibody described herein as 4A10.

In specific embodiments, the present invention provides isolated antibody molecules which include heavy and light chain variable regions having sequences set forth in (i) SEQ ID NO:1 and SEQ ID NO:5, respectively; (ii) SEQ ID NO:13 and SEQ ID NO:17, respectively; or (iii) SEQ ID NO:21 and SEQ ID NO:17, respectively; or equivalents thereof characterized as having one or more conservative amino acid substitutions. Specific embodiments are said antibodies which exhibit at last one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCs.

In particular embodiments, the present invention provides isolated IL-13Rα1 antibody molecules which include variable heavy CDR3 sequence selected from the group consisting of: SEQ ID NO:4, SEQ ID NO:12, SEQ ID NO:16 and SEQ ID NO:23; and conservative modifications thereof, which exhibit at least one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCs. Specific embodiments provide isolated antibody molecules which include a heavy chain variable region, wherein CDR1, CDR2, and/or CDR3 sequences are set forth as (i) SEQ ID NO:2, SEQ ID NO:3 and/or SEQ ID NO:4, respectively; (ii) SEQ ID NO:10, SEQ ID NO:11 and/or SEQ ID NO:12, respectively; (iii) SEQ ID NO:14, SEQ ID NO:15 and/or SEQ ID NO:16; or (iv) SEQ ID NO:22, SEQ ID NO:15 and/or SEQ ID NO:23, respectively; or equivalents thereof characterized as having one or more conservative amino acid substitutions in any one or more of the CDR sequences.

In particular embodiments, the present invention provides isolated IL-13Rα1 antibody molecules which include variable light CDR3 sequence selected from the group consisting of: SEQ ID NO:8 or SEQ ID NO:20; and conservative modifications thereof, which exhibit at least one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCs. Specific embodiments provide isolated antibody molecules which include a light chain variable region wherein CDR1, CDR2, and/or CDR3 sequences are set forth as: (i) SEQ ID NO:6, SEQ ID NO:7 and/or SEQ ID NO:8, respectively; or (ii) SEQ ID NO:18, SEQ ID NO:19 and/or SEQ ID NO:20, respectively; or an equivalent thereof characterized as having one or more conservative amino acid substitutions in any one or more of the CDR sequences.

In particular embodiments, the present invention provides isolated IL-13Rα1 antibody molecules which include heavy chain variable region CDR3 sequence and light chain variable region CDR3 sequence as set forth in: (i) SEQ ID NO:4 and SEQ ID NO:8, respectively; (ii) SEQ ID NO:16 and SEQ ID NO:20, respectively; or (iii) SEQ ID NO:23 and SEQ ID NO:20, respectively; or conservative modifications thereof in any one or more of the CDR3 sequences, that exhibit at least one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCs.

Specific embodiments provide isolated IL-13Rα1 antibody molecules which include heavy chain variable region CDR1, CDR2, and CDR3 sequences and light chain variable region CDR1, CDR2, and CDR3 sequences as set forth in: (i) SEQ ID NO:2, SEQ ID NO:3, SEQ ID NO:4, SEQ ID NO:6, SEQ ID NO:7 and SEQ ID NO:8, respectively; (ii) SEQ ID NO:14; SEQ ID NO:15; SEQ ID NO:16; SEQ ID NO:18, SEQ ID NO:19 and SEQ ID NO:20, respectively; or (iii) SEQ ID NO:22, SEQ ID NO:15, SEQ ID NO:23, SEQ ID NO:18, SEQ ID NO:19 and SEQ ID NO:20, respectively; and equivalents thereof characterized as having one or more conservative amino acid substitutions in any one or more of the CDR sequences.

Conservative amino acid substitutions, as one of ordinary skill in the art will appreciate, are substitutions that replace an amino acid residue with one imparting similar or better (for the intended purpose) functional and/or chemical characteristics. For example, conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagines, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Such modifications do not significantly reduce or alter the binding or functional inhibition characteristics of the antibody containing the amino acid sequence but may improve such properties. The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis as discussed in, for example, MacLennan et al., 1998 *Acta Physiol. Scand. Suppl.* 643:55-67, and Sasaki et al., 1998 *Adv. Biophys.* 35:1-24. The altered antibody molecules are then tested for retained or better function using functional assays available in the art or described herein. Antibody molecules possessing one or more such conservative amino acid substitutions which retain the ability to selectively bind to hIL-13Rα1 and antagonize IL-13Rα1 functioning at a level the same or better than the molecule not possessing such amino acid alterations are referred to herein as "functional equivalents" of the disclosed antibodies and form specific embodiments of the present invention.

In particular embodiments, the present invention provides isolated antibody molecules that antagonize IL-13Rα1 function (IL-13Rα1-mediated activity) and which exhibit an equilibrium dissociation constant ($K_D$) with hIL-13Rα1 which is less than 250 μM, and preferably less than 100 μM, as determined by surface plasmon resonance technologies readily available and understood by those of skill in the art, including but not limited to, BIACORE™ (Upsala, Sweden) and KINEXA® (Sapidyne Instruments, Boise, Id.) or suitable equivalent thereof. In specific embodiments, the isolated antibody molecules exhibit the above $K_D$ as well as one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCs.

In specific embodiments, the present invention provides isolated antibody molecules that include a light chain variable region which has a sequence selected from the group consisting of: SEQ ID NO:53, SEQ ID NO:54, SEQ ID NO:55, SEQ ID NO:56, SEQ ID NO:57, SEQ ID NO:58 and SEQ ID NO:64; equivalents characterized as having one or more conservative amino acid substitutions, and homologs thereof. In particular embodiments, isolated antibody molecules are provided that have (i) a heavy chain variable region which includes a sequence selected from the group consisting of: SEQ ID NO:13 and SEQ ID NO:21 and (ii) a light chain variable region which includes a sequence selected from the group consisting of: SEQ ID NO:53, SEQ ID NO:54, SEQ ID NO:55, SEQ ID NO:56, SEQ ID NO:57, SEQ ID NO:58 and SEQ ID NO:64; equivalents characterized as having one or more conservative amino acid substitutions, and homologs thereof.

In specific embodiments, the present invention provides isolated antibody molecules which exhibit the above $K_D$, antagonize IL-13Rα1-mediated activity, and include a light chain variable region having a complementarity determining region 3 (CDR3) domain selected from the group consisting of: SEQ ID NO:24, SEQ ID NO:25, SEQ ID NO:26, SEQ ID NO:27, SEQ ID NO:28, SEQ ID NO:29 and SEQ ID NO:63; or an equivalent thereof characterized as having conservative amino acid substitutions; specific embodiments of which have the conservative amino acid substitutions at positions 1, 2, 4 and/or 5 of SEQ ID NO:20. In particular embodiments, isolated antibody molecules are provided that include (i) a heavy chain variable region which has a CDR3 domain selected from the group consisting of: SEQ ID NO:16 and SEQ ID NO:23 and (ii) a light chain variable region which has a CDR3 domain selected from the group consisting of: SEQ ID NO:24, SEQ ID NO:25, SEQ ID NO:26, SEQ ID NO:27, SEQ ID NO:28, SEQ ID NO:29 and SEQ ID NO:63; equivalents characterized as having one or more conservative amino acid substitutions, and homologs thereof.

Specific embodiments provide isolated antibody molecules which include (i) a heavy chain variable region having CDR1, CDR2, and CDR3 sequences comprising SEQ ID NO:22, SEQ ID NO:15 and SEQ ID NO:23, respectively; and (ii) a light chain variable region having CDR1, CDR2, and CDR3 sequences selected from the group consisting of: (a) SEQ ID NO:18, SEQ ID NO:19 and SEQ ID NO:24, respectively; (b) SEQ ID NO:18, SEQ ID NO:19 and SEQ ID NO:25, respectively; (c) SEQ ID NO:18, SEQ ID NO:19 and SEQ ID NO:26, respectively; (d) SEQ ID NO:18, SEQ ID NO:19 and SEQ ID NO:27, respectively, (e) SEQ ID NO:18, SEQ ID NO:19 and SEQ ID NO:28, respectively; (f) SEQ ID NO:18, SEQ ID NO:19 and SEQ ID NO:29, respectively; and (g) SEQ ID NO:18, SEQ ID NO:19 and SEQ ID NO:63, respectively; or an equivalent thereof characterized as having one or more conservative amino acid substitutions in any one or more of the CDR sequences.

Specific embodiments provide isolated antibody molecules which include (i) a heavy chain variable region having CDR1, CDR2, and CDR3 sequences comprising SEQ ID NO:14, SEQ ID NO:15 and SEQ ID NO:16, respectively; and (ii) a light chain variable region having CDR1, CDR2, and CDR3 sequences selected from the group consisting of: (a) SEQ ID NO:18, SEQ ID NO:19 and SEQ ID NO:24, respectively; (b) SEQ ID NO:18, SEQ ID NO:19 and SEQ ID NO:25, respectively; (c) SEQ ID NO:18, SEQ ID NO:19 and SEQ ID NO:26, respectively; (d) SEQ ID NO:18, SEQ ID NO:19 and SEQ ID NO:27, respectively, (e) SEQ ID NO:18, SEQ ID NO:19 and SEQ ID NO:28, respectively; (f) SEQ ID NO:18, SEQ ID NO:19 and SEQ ID NO:29, respectively; and (g) SEQ ID NO:18, SEQ ID NO:19 and SEQ ID NO:63, respectively; or an equivalent thereof characterized as having one or more conservative amino acid substitutions in any one or more of the CDR sequences.

In another aspect, the present invention provides antibody molecules which include heavy and/or light chain variable regions with amino acid sequences that are homologous to the corresponding amino acid sequences of the disclosed antibodies, wherein the antibody molecules exhibit an equilibrium dissociation constant ($K_D$) of less than 20 nM with human interleukin 13 receptor α1 (hIL-13Rα1) and antagonize hIL-13Rα1-mediated activity. Specific embodiments are antibody molecules which include heavy and/or light chain variable regions which are at least 90% homologous to disclosed heavy and/or light chain variable regions, respectively, that exhibit at least one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCs. Other embodiments of the present invention are antibody molecules which include heavy and/or light chain variable regions which are at least 90% homologous to disclosed heavy and/or light chain variable regions, respectively, that compete for binding to hIL-13Rα1 with an antibody as produced by the hybridoma cell lines deposited as ATCC Deposit Nos. PTA-6932 (2B6), PTA-6930 (6C11), and PTA-6934 (8B4); or an antibody described herein as 4A10. Reference to "at least 90% homologous" in variable regions includes at least 90, 91, 92, 93, 94, 95, 96, 97, 98, 99 and 100% homologous sequences.

Antibodies with amino acid sequences homologous to the amino acid sequences of the specific antibody molecules described herein are typically produced to improve one or more of the properties of the antibody without changing its specificity for IL-13Rα1. One method of obtaining such sequences, which is not the only method available to the skilled artisan, is to mutate sequence encoding heavy and/or light chain variable regions disclosed herein by site-directed or random mutagenesis, express an antibody molecule comprising the mutated variable region(s), and test the encoded antibody molecule for retained function using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and length of each gap, which need to be introduced for optimal alignment of the two sequences. The comparison of sequences and determination of percent identity between sequences can be determined using methods generally known to those in the art and can be accomplished using a mathematical algorithm. For example, the percent identity between amino acid sequences and/or nucleotide sequences can be determined using the algorithm of Meyers and Miller, 1988 *Comput. Appl. Biosci.* 4:11-17, which has been incorporated into the ALIGN program (version 2.0). In addition, the percent identity between amino acid sequences or nucleotide sequences can be determined using the GAP program in the GCG software package available online from Accelrys, using its default parameters.

In one embodiment, the present invention provides an isolated antibody molecule including a heavy chain variable region sequence that is at least 90% homologous to a sequence selected from the group consisting of: SEQ ID NO:1, SEQ ID NO:9, SEQ ID NO:13 and SEQ ID NO:21. In another embodiment, the present invention provides an isolated antibody molecule including a light chain variable region sequence that is at least 90% homologous to a sequence selected from the group consisting of: SEQ ID NO:5, SEQ ID NO:17, SEQ ID NO:53, SEQ ID NO:54, SEQ ID NO:55, SEQ ID NO:56, SEQ ID NO:57, SEQ ID NO:58 and SEQ ID NO:64. In specific embodiments, the present invention provides an isolated antibody molecule which includes heavy and light chain variable regions that are at least 90% homologous to (i) SEQ ID NOs: 1 and 5, respectively; (ii) SEQ ID NOs: 13 and 17, respectively; and (iii) SEQ ID NOs: 21 and 17, respectively.

One method by which one skilled in the art could obtain an antibody having $V_H$ and/or $V_L$ sequences having high (i.e., 90% or greater) homology to the $V_H$ sequences and/or the $V_L$ sequences described herein is by mutagenesis (e.g., site-directed or random mutagenesis) of nucleic acid molecules encoding SEQ ID NOs: 1, 9, 13 and 21 and/or SEQ ID NOs: 5, 17, 53, 54, 55, 56, 57, 58 and 64, followed by testing the encoded altered antibody for retained function using the functional assays described herein. For example, comparing the sets of heavy and light chain variable regions CDR1, CDR2 and CDR3 sequences, each of the optimized antibodies derived from 8B4 described in the Examples are at least 90% homologous to 8B4. Alternatively, homologous antibodies may be obtained through other antibody isolation approaches. For example, the set of heavy chain variable region CDRs of 6C11 are at least 90% homologous to those of 8B4. The homology over the entire heavy chain variable region is even greater.

In yet another embodiment, the present invention provides isolated antibody molecules including heavy and/or light chain variable regions having sets of CDR1, CDR2 and CDR3 sequences that are homologous to the sets of CDR1, CDR2 and CDR3 sequences of the antibodies disclosed herein, and wherein the antibodies retain the desired functional properties of the anti-hIL-13Rα1 antibodies of the invention. For example, the present invention provides an isolated antibody molecule including a heavy chain variable region with a set of CDR1, CDR2 and CDR3 sequences that are at least 90% homologous to a set of CDR1, CDR2 and CDR 3 sequences selected from the group consisting of: (i) SEQ ID NOs: 2, 3 and 4, respectively; (ii) SEQ ID NOs: 10, 11 and 12, respectively, (iii) SEQ ID NOs: 14, 15 and 16; and (iv) SEQ ID NOs: 22, 15 and 23. In specific embodiments, the present invention provides an isolated antibody molecule which includes a set of heavy CDR 1, 2 and 3 and light CDR 1, 2 and 3 sequences that are at least 90% homologous to a set of heavy CDR 1, 2 and 3 and light CDR 1, 2 and 3 sequences that are SEQ ID NOs: 2, 3, 4, 6, 7 and 8, respectively. In another embodiment, the present invention provides isolated antibody molecules which include (a) a heavy chain variable region with a set of CDR1, CDR2 and CDR3 sequences that are at least 90% homologous to a set of CDR1, CDR2 and CDR3 sequences selected from the group consisting of: (i) SEQ ID NO:14, SEQ ID NO:15 and SEQ ID NO:16, respectively and (ii) SEQ ID NO:22, SEQ ID NO:15 and SEQ ID NO:23, respectively; and (b) a light chain variable region with a set of CDR1, CDR2 and CDR3 sequences that are at least 90% homologous to a set of CDR1, CDR2 and CDR3 sequences selected from the group consisting of: (i) SEQ ID NO:18, SEQ ID NO:19 and SEQ ID NO:20, respectively; (ii) SEQ ID NO:18, SEQ ID NO:19 and SEQ ID NO:24, respectively; (b) SEQ ID NO:18, SEQ ID NO:19 and SEQ ID NO:25, respectively; (c) SEQ ID NO:18, SEQ ID NO:19 and SEQ ID NO:26, respectively; (d) SEQ ID NO:18, SEQ ID NO:19 and SEQ ID NO:27, respectively, (e) SEQ ID NO:18, SEQ ID NO:19 and SEQ ID NO:28, respectively; (f) SEQ ID NO:18, SEQ ID NO:19 and SEQ ID NO:29, respectively; and (g) SEQ ID NO:18, SEQ ID NO:19 and SEQ ID NO:63, respectively.

Specific antibodies of the present invention inhibit the binding of IL-13 to hIL-13Rα1. Specific antibodies of the present invention compete for binding to hIL-13Rα1 with any of the antibodies disclosed herein and, particularly, 2B6, 4A10, 6C11, and/or 8B4. Such competing antibodies can be identified based on their ability to cross-compete (e.g., to competitively inhibit the binding of, in a statistically significant manner) with 2B6, 4A10, 6C11, 8B4, or its derivatives disclosed herein in standard IL-13Rα1 binding assays. The ability of a test antibody to inhibit the binding of 2B6, 4A10, 6C11, and/or 8B4 or derivative to human IL-13Rα1 demonstrates that the test antibody can compete with that antibody for binding to human IL-13Rα1. Such an antibody may, according to non-limiting theory, bind to the same or a related (e.g., a structurally similar or spatially proximal) epitope on human IL-13Rα1 as the antibody with which it competes. Antibodies that compete for binding with 2B6, 4A10, 6C11, 8B4 or its disclosed derivatives may then be assessed for having at least one of the following functional properties: (i) inhibition of IL-13-induced eotaxin release in NHDF cells; (ii) inhibition of IL-13-induced STAT6 phosphorylation in NHDF cells; or (iii) inhibition of IL-13-stimulated release of TARC in blood or PBMCS. In specific embodiments, the antibodies are human antibodies.

Manipulation of monoclonal and other antibodies to produce other antibodies or chimeric molecules which retain the specificity of the original antibody is well within the realm of one skilled in the art. This can be accomplished, for example, using techniques of recombinant DNA technology. Such techniques may involve the introduction of DNA encoding the immunoglobulin variable region, or one or more of the CDRs, of an antibody to the variable region, constant region, or constant region plus framework regions, as appropriate, of a different immunoglobulin. Such molecules form important aspects of the present invention. Specific immunoglobulins, into which the disclosed sequences may be inserted or, in the alternative, form the essential part of, include but are not limited to the following antibody molecules which form particular embodiments of the present invention: a Fab (monovalent fragment with variable light ($V_L$), variable heavy ($V_H$), constant light ($C_L$) and constant heavy 1 ($C_{H1}$) domains), a F(ab')$_2$ (bivalent fragment comprising two Fab fragments linked by a disulfide bridge or alternative at the hinge region), a Fd ($V_H$ and $C_{H1}$ domains), a Fv ($V_L$ and $V_H$ domains), a scFv (a single chain Fv where $V_L$ and $V_H$ are joined by a linker, e.g., a peptide linker, see, e.g., Bird et al., 1988 *Science* 242:423-426, Huston et al., 1988 *Proc. Natl. Acad. Sci. USA* 85:5879-5883), a bispecific antibody molecule (an antibody molecule comprising an IL-13Rα1-specific antibody or antigen binding fragment as disclosed herein linked to a second functional moiety having a different binding specificity than the antibody, including, without limitation, another peptide or protein such as an antibody, or receptor ligand), a bispecific single chain Fv dimer (see, e.g., PCT/US92/09965), an isolated CDR3, a minibody (single chain-CH3 fusion that self assembles into a bivalent dimer of about 80 kDa), a 'scAb' (an antibody fragment containing $V_H$ and $V_L$, as well as either $C_L$ or $C_{H1}$), a dAb fragment ($V_H$ domain, see, e.g., Ward et al., 1989 Nature 341:544-546, and McCafferty et al., 1990 Nature 348:552-554; or $V_L$ domain; Holt et al., 2003 Trends in Biotechnology 21:484-489), a diabody (see, e.g., Holliger et al., 1993 Proc. Natl. Acad. Sci. USA 90:6444-6448 and WO 94/13804), a triabody, a tetrabody, a minibody (a scFv joined to a CH3; see, e.g., Hu et al., 1996 Cancer Res. 56:3055-3061), IgG, IgG1, IgG2, IgG3, IgG4, IgM, IgD, IgA, IgE or any derivatives thereof, and artificial antibodies based upon protein scaffolds, including but not limited to fibronectin type III polypeptide antibodies (see, e.g., U.S. Pat. No. 6,703,199 and WO 02/32925) or cytochrome B; see, e.g., Koide et al., 1998 J. Molec. Biol. 284:1141-1151, and Nygren et al., 1997 Current Opinion in Structural Biology 7:463-469. Certain antibody molecules including, but not limited to, Fv, scFv, and diabody molecules may be stabilized by incorporating disulfide bridges to line the $V_H$ and $V_L$ domains, see, e.g., Reiter et al., 1996 Nature Biotech. 14:1239-1245. Bispecific antibodies may be produced using conventional technologies (see, e.g., Holliger & Winter, 1993 Current Opinion Biotechnol. 4:446-449, specific methods of which include production chemically, or from hybrid hybridomas) and other technologies including, but not limited to, the BITE™ technology (molecules possessing antigen binding regions of different specificity with a peptide linker) and knobs-into-holes engineering (see, e.g., Ridgeway et al., 1996 Protein Eng. 9:616-621). Bispecific diabodies may be produced in E. coli, and these molecules, as well as other antibody molecules, as one of skill in the art will appreciate, may be selected using phage display in the appropriate libraries (see, e.g., WO 94/13804).

Variable domains, into which CDRs of interest are inserted, may be obtained from any germ-line or rearranged human variable domain. Variable domains may also be synthetically produced. The CDR regions can be introduced into the respective variable domains using recombinant DNA technology. One means by which this can be achieved is described in Marks et al., 1992 Bio/Technology 10:779-783. Expression and selection may be achieved using suitable technologies including, but not limited to phage display (see, e.g., WO 92/01047, Kay et al., 1996 Phage Display of Peptides and Proteins: A Laboratory Manual, San Diego: Academic Press), yeast display, bacterial display, T7 display, and ribosome display (see, e.g., Lowe & Jermutus, 2004 Curr. Pharm. Biotech. 517-527). Specific embodiments provide the CDR(s) in germline framework regions. Specific embodiments herein provide heavy chain CDRs 1, 2 and/or 3 of SEQ ID NOs: 2, 3, and 4, respectively, into VH-33 (JH2); with additional embodiments thereof additionally comprising light chain CDRs 1, 2 and/or 3 of SEQ ID NOs: 6, 7 and 8, respectively, provided in Vk1-L4 (Jk2). Specific embodiments herein provide heavy chain CDRs 1, 2 and/or 3 of SEQ ID NOs: 10, 11, and 12, respectively, into VH-30.3 (JH6). Specific embodiments herein provide heavy chain CDRs 1, 2 and/or 3 of SEQ ID NOs: 14, 15, and 16, respectively, into VH3-23 (JH2); with additional embodiments thereof additionally including light chain CDRs 1, 2 and/or 3 of SEQ ID NOs: 18, 19 and 20, respectively, provided in Vk6-A26(Jk2). Specific embodiments herein provide heavy chain CDRs 1, 2 and/or 3 of SEQ ID NOs: 22, 15, and 23, respectively, into VH3-23 (JH2); with additional embodiments thereof additionally comprising light chain CDRs 1, 2 and/or 3 of SEQ ID NOs: 18, 19 and 20, respectively, provided in Vk6-A26(Jk2). Particular embodiments herein provide heavy chain CDRs 1, 2 and/or 3 of either (i) SEQ ID NOs: 22, 15, and 23, respectively, or (ii) SEQ ID NOs: 14, 15, and 16, respectively; into VH3-23 (JH2); with additional embodiments thereof additionally include a light chain CDR 1 of SEQ ID NO:18, a CDR2 of SEQ ID NO:19 and/or a CDR3 selected from the group consisting of: SEQ ID NOs: 24, 25, 26, 27, 28, 29 and 63; respectively; provided in Vk6-A26(Jk2). In specific embodiments, a variable heavy domain is paired with a variable light domain to provide an antigen binding site. Alternatively, independent regions (e.g., a variable heavy domain alone) may be used to bind antigen. The artisan is well aware, as well, that two domains of an Fv fragment, $V_L$ and $V_H$, while perhaps coded by separate genes, may be joined, using recombinant methods, by a synthetic linker that enables them to be made as a single protein chain in which the $V_L$ and $V_H$ regions pair to form monovalent molecules (scFvs).

The present invention encompasses antibody molecules that are human, humanized, deimmunized, chimeric and primatized. The invention also encompasses antibodies produced by the process of veneering; see, e.g., Mark et al., 1994 Handbook of Experimental Pharmacology, vol. 113: The pharmacology of monoclonal Antibodies, Springer-Verlag, pp. 105-134 and U.S. Pat. No. 6,797,492. "Human" in reference to the disclosed antibody molecules specifically refers to antibody molecules having variable and/or constant regions derived from human germline immunoglobulin sequences, wherein said sequences may, but need not, be modified/altered to have certain amino acid substitutions or residues that are not encoded by human germline immunoglobulin sequence. Such mutations can be introduced by methods including, but not limited to, random or site-specific mutagenesis in vitro, or by somatic mutation in vivo. Specific examples of mutation techniques discussed in the literature are that disclosed in Gram et al., 1992 Proc. Natl. Acad. Sci. USA 89:3576-3580; Barbas et al., 1994 Proc. Natl. Acad. Sci. USA 91:3809-3813, and Schier et al., 1996 J. Mol. Biol. 263:551-567. These are only specific examples and do not represent the only available techniques. There are a plethora of mutation techniques in the scientific literature which are available to, and widely appreciated by, the skilled artisan. "Humanized" in reference to the disclosed antibody molecules refers specifically to antibody molecules wherein CDR sequences derived from another mammalian species, such as a mouse, are grafted onto human framework sequences. "Primatized" in reference to the disclosed antibody molecules refers to antibody molecules wherein CDR sequences of a non-primate are inserted into primate framework sequences, see, e.g., WO 93/02108 and WO 99/55369.

Specific antibodies of the present invention are monoclonal antibodies and, in particular embodiments, are in one of the following antibody formats: IgD, IgA, IgE, IgM, IgG1, IgG2, IgG3, IgG4 or any derivative of any of the foregoing. The language "derivatives thereof" or "derivatives" includes, inter alia, (i) antibodies and antibody molecules with modifications in the framework or CDR regions of one or both variable regions (i.e., $V_H$ and/or $V_L$), (ii) antibodies and antibody molecules with manipulations in the constant regions of the heavy and/or light chains, and (iii) antibodies and antibody molecules that contain additional chemical moieties which are not normally a part of the immunoglobulin molecule (e.g., pegylation).

Manipulations of the variable regions can be within one or more of the $V_H$ and/or $V_L$ CDR regions. Site-directed mutagenesis or random mutagenesis can be performed to introduce the mutation(s) and the effect on antibody functional property of interest can be evaluated using can be evaluated by available in vitro or in vivo assays including those described herein.

Antibodies of the present invention also include those in which modifications have been made to the framework residues within $V_H$ and/or $V_L$ to improve one or more properties of the antibody of interest. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, where present, typically to alter one or more functional properties of the antibody, such as serum half-life, complement fixation, Fc receptor binding, and/or antigen-dependent cellular cytotoxicity.

In one embodiment, the hinge region of $C_{H1}$ is modified such that the number of cysteine residues in the hinge region is altered, e.g., increased or decreased, to, for example, facilitate assembly of the light and heavy chains or to increase or decrease the stability of the antibody. This approach is described further in U.S. Pat. No. 5,677,425 by Bodmer et al.

In another embodiment, the Fc hinge region of an antibody is mutated to decrease the biological half-life of the antibody. This approach is described in further detail in U.S. Pat. No. 6,165,745 by Ward et al.

In another embodiment, the antibody is modified to increase its biological half-life. Various approaches are possible. For example, one or more of the following mutations can be introduced: Thr252Leu, Thr254Ser, Thr256Phe, as described in U.S. Pat. No. 6,277,375 by Ward. Alternatively, to increase the biological half-life, the antibody can be altered within the $C_{H1}$ or CL region to contain a salvage receptor binding epitope taken from two loops of a $C_{H2}$ domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, see U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are modified to thereby alter the ability of the antibody to fix complement. This approach is described further in WO 94/29351 by Bodmer et al.

In yet another example, the Fc region is modified to increase the ability of the antibody to mediate antibody-dependent cellular cytotoxicity (ADCC) and/or to increase the affinity of the antibody for an Fcγ receptor by modifying one or more amino acids; see for example WO 00/42072 by Presta. Moreover, the binding sites on human IgG1 for FcγR1, FcγRII, FcγRIII and FcRn have been mapped and variants with improved binding have been described (see Shields et al, J. Biol. Chem. 276:6591-6604, 2001).

The concept of generating "hybrids" or "combinatorial" IgG forms including various antibody isotypes to hone in on desired effector functionality has generally been described; see, e.g., Tao et al., 1991 J. Exp. Med. 173:1025-1028. A specific embodiment of the present invention encompasses antibody molecules that possess specific manipulations in the Fc region which have been found to result in reduced binding to FcγR receptors or C1q on the part of the antibody. The present invention, therefore, encompasses antibodies in accordance with the present description that do not provoke (or provoke to a lesser extent) antibody-dependent cellular cytotoxicity (ADCC), complement-mediated cytotoxicity (CMC), or form immune complexes, while retaining normal pharmacokinetic (PK) properties. Specific embodiments of the present invention provide an antibody molecule as defined in accordance with the present invention which includes, as part of its immunoglobulin structure, the sequence set forth in SEQ ID NO:79. FIG. 2 illustrates a comparison of the sequence of IgG2 m4 (as described in U.S. Patent Publication No. US20070148167(A1)), which contains the sequence set forth in SEQ ID NO:79, with the amino acid sequence of IgG1, IgG2, and IgG4.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation.

Specific antibody molecules may carry a detectable label, or may be conjugated to a toxin (e.g., a cytotoxin), a radioactive isotope, a radionuclide, a liposome, a targeting moiety, a biosensor, a cationic tail, or an enzyme (e.g., via a peptidyl bond or linker). Such antibody molecule compositions form an additional aspect of the present invention.

In another aspect, the present invention provides isolated nucleic acid encoding the disclosed antibody molecules. The nucleic acid may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, for example, using standard techniques, including without limitation, alkaline/SDS treatment, CsCl banding, column chromatography, agarose gel electrophoresis and other suitable methods known in the art. The nucleic acid may include DNA (inclusive of cDNA) and/or RNA. Nucleic acids of the present invention can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

The present invention encompasses isolated nucleic acid encoding the disclosed variable heavy and/or light chains and select components thereof, particularly the disclosed respective CDR3 regions. In specific embodiments hereof, the CDR(s) are provided within antibody framework regions. Specific embodiments provide isolated nucleic acid encoding the CDR(s) into the germline framework regions. The isolated nucleic acid encoding the variable regions can be provided within any desired antibody molecule format including, but not limited to, the following: F(ab')$_2$, a Fab, a Fv, a scFv, bispecific antibody molecules (antibody molecules including an IL-13Rα1-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, a dAb fragment, diabody, triabody or tetrabody, a minibody, IgG, IgG1, IgG2, IgG3, IgG4, IgM, IgD, IgA, IgE or any derivatives thereof.

Specific embodiments provide isolated nucleic acid encoding antibody molecules including a heavy chain variable domain; which has a nucleic acid sequence selected from the group consisting of: SEQ ID NO:30, SEQ ID NO:38, SEQ ID NO:42 and SEQ ID NO:50. Specific embodiments of the present invention provide isolated nucleic acid encoding antibody molecules including heavy chain CDR1, CDR2 and/or CDR3 sequence; which has a nucleic acid sequence selected from the group consisting of: (i) SEQ ID NO:31, SEQ ID NO:32 and/or SEQ ID NO:33, respectively; (ii) SEQ ID NO:39, SEQ ID NO:40 and/or SEQ ID NO:41, respectively; (iii) SEQ ID NO:39, SEQ ID NO:40 and/or SEQ ID NO:83, respectively; (iv) SEQ ID NO:43, SEQ ID NO:44 and/or SEQ ID NO:45, respectively; (v) SEQ ID NO:43, SEQ ID NO:44 and/or SEQ ID NO:84, respectively; or (vi) SEQ ID NO:51, SEQ ID NO:44 and/or SEQ ID NO:52, respectively.

Specific embodiments provide isolated nucleic acid encoding antibody molecules including a light chain variable domain, which has a nucleic acid sequence selected from the group consisting of: SEQ ID NO:34 SEQ ID NO:46, SEQ ID NO:66, SEQ ID NO:68, SEQ ID NO:70, SEQ ID NO:72 and SEQ ID NO:74. Specific embodiments of the present invention provide isolated nucleic acid encoding antibody molecules including light chain CDR1, CDR2 and/or CDR3 sequence; which has a nucleic acid sequence selected from the group consisting of: (i) SEQ ID NO:35, SEQ ID NO:36 and/or SEQ ID NO:37, respectively; (ii) SEQ ID NO:47, SEQ ID NO:48 and/or SEQ ID NO:49, respectively; (iii) SEQ ID NO:47, SEQ ID NO:48 and/or SEQ ID NO:65, respectively; (iv) SEQ ID NO:47, SEQ ID NO:48 and/or SEQ ID NO:67, respectively; (v) SEQ ID NO:47, SEQ ID NO:48 and/or SEQ ID NO:69, respectively; (vi) SEQ ID NO:47, SEQ ID NO:48 and/or SEQ ID NO:71, respectively; (vii) SEQ ID NO:47, SEQ ID NO:48 and/or SEQ ID NO:73, respectively.

Specific embodiments of the present invention encompass nucleic acid encoding antibody molecules that possess manipulations in the Fc region which result in reduced binding to FcγR receptors or Clq on the part of the antibody. One specific embodiment of the present invention is isolated nucleic acid with a sequence as set forth in SEQ ID NO:80. In specific embodiments, synthetic antibody molecules can be produced by expression from nucleic acid generated from oligonucleotides synthesized and assembled within suitable expression vectors; see, e.g., Knappick et al., 2000 *J. Mol. Biol.* 296:57-86, and Krebs et al., 2001 *J. Immunol. Methods* 254:67-84.

Also included within the present invention are nucleic acids including nucleotide sequences which are at least about 90% identical and more preferably at least about 95% identical to the nucleotide sequences described herein, and which nucleotide sequences encode antibodies of the present invention. Sequence comparison methods to determine identity are known to those skilled in the art and include those discussed earlier. Reference to "at least about 90% identical" includes at least about 90, 91, 92, 93, 94, 95, 96, 97, 98, 99 or 100% identical.

The invention further provides nucleic acids that hybridize to the complement of nucleic acid disclosed herein (e.g., the complement of nucleic acid including (i) $V_H$ nucleotide sequence SEQ ID NO:30, SEQ ID NO:38, SEQ ID NO:42 or SEQ ID NO:50; (ii) heavy chain CDR1, CDR2 and/or CDR3 nucleotide sequence selected from the group consisting of: (a) SEQ ID NO:31, SEQ ID NO:32 and/or SEQ ID NO:33, respectively; (b) SEQ ID NO:39, SEQ ID NO:40 and/or SEQ ID NO:41, respectively; (c) SEQ ID NO:39, SEQ ID NO:40 and/or SEQ ID NO:83, respectively; (d) SEQ ID NO:43, SEQ ID NO:44 and/or SEQ ID NO:45, respectively; (e) SEQ ID NO:43, SEQ ID NO:44 and/or SEQ ID NO:84, respectively; or (f) SEQ ID NO:51, SEQ ID NO:44 and/or SEQ ID NO:52, respectively; (iii) $V_L$ nucleotide sequence SEQ ID NO:34 SEQ ID NO:46, SEQ ID NO:66, SEQ ID NO:68, SEQ ID NO:70, SEQ ID NO:72 or SEQ ID NO:74; (iv) light chain CDR1, CDR2 and/or CDR3 nucleotide sequence selected from the group consisting of: (a) SEQ ID NO:35, SEQ ID NO:36 and/or SEQ ID NO:37, respectively; (b) SEQ ID NO:47, SEQ ID NO:48 and/or SEQ ID NO:49, respectively; (c) SEQ ID NO:47, SEQ ID NO:48 and/or SEQ ID NO:65, respectively; (d) SEQ ID NO:47, SEQ ID NO:48 and/or SEQ ID NO:67, respectively; (e) SEQ ID NO:47, SEQ ID NO:48 and/or SEQ ID NO:69, respectively; (f) SEQ ID NO:47, SEQ ID NO:48 and/or SEQ ID NO:71, respectively; or (g) SEQ ID NO:47, SEQ ID NO:48 and/or SEQ ID NO:73, respectively; and (v) nucleic acid sequence as described herein which encode disclosed antibody molecules) under particular hybridization conditions, which nucleic acids encode antibody molecules that bind specifically to hIL-13Rα1 and antagonize IL-13Rα1-mediated activity. Methods for hybridizing nucleic acids are well-known in the art; see, e.g., Ausubel, *Current Protocols in Molecular Biology*, John Wiley & Sons, N.Y., 6.3.1-6.3.6, 1989. As defined herein, moderately stringent hybridization conditions may use a pre-washing solution containing SX sodium chloride/sodium citrate (SSC), 0.5% w/v SDS, 1.0 mM EDTA (pH 8.0), hybridization buffer of about 50% v/v formamide, 6×SSC, and a hybridization temperature of 55° C. (or other similar hybridization solutions, such as one containing about 50% v/v formamide, with a hybridization temperature of 42° C.), and washing conditions of 60° C., in 0.5×SSC, 0.1% w/v SDS. A stringent hybridization condition may be at 6×SSC at 450C, followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98, or 99% identical to each other typically remain hybridized to each other. The basic parameters affecting the choice of hybridization conditions and guidance for devising suitable conditions are set forth by Sambrook et al., *Molecular Cloning: A Laboratory Manual*, Cold Spring Harbor Laboratory Press, Cold Spring Harbor, N.Y., chapters 9 and 11, 1989 and Ausubel et al. (eds), *Current Protocols in Molecular Biology*, John Wiley & Sons, Inc., sections 2.10 and 6.3-6.4, 1995, and can be readily determined by those having ordinary skill in the art based on, for example, the length and/or base composition of the DNA.

The present invention provides isolated antibodies which comprise a light and/or heavy chain variable domain that is encoded at least in part by a nucleotide sequence that hybridizes under moderately stringent conditions to the complement of a nucleic acid sequence encoding a light and/or heavy chain variable domain disclosed herein (e.g., selected from the group consisting of: SEQ ID NO:30, SEQ ID NO:38, SEQ ID NO:42, SEQ ID NO:50, SEQ ID NO:34 SEQ ID NO:46, SEQ ID NO:66, SEQ ID NO:68, SEQ ID NO:70, SEQ ID NO:72 and SEQ ID NO:74). In another embodiment, the present invention encompasses isolated antibodies which include a light and/or heavy chain variable domain that is encoded at least in part by a nucleotide sequence that hybridizes under stringent conditions to the complement of a nucleic acid sequence with a light and/or heavy chain variable domain disclosed herein.

In another aspect, the present invention provides vectors including said nucleic acid. Vectors in accordance with the present invention include, but are not limited to, plasmids and other expression constructs (e.g., phage or phagemid, as appropriate) suitable for the expression of the desired antibody molecule at the appropriate level for the intended purpose; see, e.g., Sambrook & Russell, *Molecular Cloning: A Laboratory Manual:* 3$^{rd}$ Edition, Cold Spring Harbor Laboratory Press. For most cloning purposes, DNA vectors may be used. Typical vectors include plasmids, modified viruses, bacteriophage, cosmids, yeast artificial chromosomes, and other forms of episomal or integrated DNA. It is well within the purview of the skilled artisan to determine an appropriate vector for a particular gene transfer, generation of a recombinant human antibody, or other use. In specific embodiments, in addition to a recombinant gene, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, other sequences as appropriate and the potential for high copy number. Examples of expression vectors for antibody and antibody fragment production are well known in the art; see, e.g., Persic et al., 1997 *Gene* 187:9-18; Boel et al., 2000 *J. Immunol. Methods* 239: 153-166, and Liang et al., 2001 *J. Immunol. Methods* 247: 119-130. If desired, nucleic acid encoding an antibody may be integrated into the host chromosome using techniques well-known in the art; see, e.g., Ausubel, *Current Protocols in Molecular Biology*, John Wiley & Sons, 1999, and Marks et al., WO 95/17516. Nucleic acid may also be expressed on plasmids maintained episomally or incorporated into an artificial chromosome; see, e.g., Csonka et al., 2000 *J. Cell Science* 113:3207-3216; Vanderbyl et al., 2002 *Molecular Therapy* 5:10. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt-end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein). Any technique available to the skilled artisan may be employed to introduce the nucleic acid into the host cell; see, e.g., Morrison, 1985 *Science,* 229:1202. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The antibody so produced may be harvested from the host cells in conventional ways. Techniques suitable for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage).

In another aspect, the present invention provides isolated cell(s) comprising nucleic acid encoding the disclosed antibody molecules and components thereof as described. A variety of different cell lines can be used for recombinant production of antibody molecules, including but not limited to those from prokaryotic organisms (e.g., *E. coli, Bacillus*, and *Streptomyces*) and from eukaryotic (e.g., yeast, Baculovirus, and mammalian); see, e.g., Breitling et al., Recombinant antibodies, John Wiley & Sons, Inc. and Spektrum Akademischer Verlag, 1999. Plant cells, including transgenic plants, and animal cells, including transgenic animals (other than humans), comprising the nucleic acid or antibody molecules disclosed herein are also contemplated as part of the present invention. Suitable mammalian cell lines including, but not limited to, those derived from Chinese Hamster Ovary (CHO) cells, including but not limited to DHFR-CHO cells (described in Urlaub and Chasin, 1980 *Proc. Natl. Acad. Sci. USA* 77:4216-4220) used, for example, with a DHFR selectable marker (e.g., as described in Kaufman and Sharp, 1982 *Mol. Biol.* 159:601-621), NS0 myeloma cells (where a GS expression system as described in WO 87/04462, WO 89/01036, and EP 338,841 may be used), COS cells, SP2 cells, HeLa cells, baby hamster kidney cells, YB2/0 rat myeloma cells, human embryonic kidney cells, human embryonic retina cells, and others including the nucleic acid or antibody molecules disclosed herein form additional embodiments of the present invention. Specific embodiments of the present invention may employ *E. coli*; see, e.g., Plückthun, 1991 *Bio/Technology* 9:545-551, or yeast, such as

*Pichia*, and recombinant derivatives thereof (see, e.g., Li et al., 2006 *Nat. Biotechnol.* 24:210-215). Additional specific embodiments of the present invention may employ eukaryotic cells for the production of antibody molecules, see, Chadd & Chamow, 2001 *Current Opinion in Biotechnology* 12:188-194, Andersen & Krummen, 2002 *Current Opinion in Biotechnology* 13:117, Larrick & Thomas, 2001 *Current Opinion in Biotechnology* 12:411-418. Specific embodiments of the present invention may employ mammalian cells able to produce antibody molecules with proper post translational modifications. Post-translational modifications include, but are by no means limited to, disulfide bond formation and glycosylation. Another type of post translational modification is signal peptide cleavage. Specific embodiments herein have the appropriate glycosylation; see, e.g., Yoo et al., 2002 *J. Immunol. Methods* 261:1-20. Naturally occurring antibodies contain at least one N-linked carbohydrate attached to a heavy chain. Id. Different types of mammalian host cells can be used to provide for efficient post-translational modifications. Examples of such host cells include Chinese Hamster Ovary (CHO), HeLa, C6, PC12, and myeloma cells; see, Yoo et al., 2002 *J. Immunol. Methods* 261:1-20, and Persic et al., 1997 *Gene* 187:9-18.

In another aspect, the present invention provides isolated cell(s) comprising a polypeptide of the present invention.

In another aspect, the present invention provides a method of making an antibody molecule of the present invention, which involves incubating a cell harboring nucleic acid encoding a heavy and/or light chain (dictated by the desired antibody molecule) with specificity for human IL-13Rα1 under conditions that allow the expression and assembly of said heavy and/or light chains into an antibody molecule, and isolating said antibody molecule from the cell. One example by which to generate the desired heavy and/or light chain sequence is to first amplify (and modify) the germline heavy and/or light chain variable sequences using PCR. Germline sequence for human heavy and/or light variable regions are readily available to the skilled artisan, see, e.g., the "Vbase" human germline sequence database, and Kabat, E. A. et al., 1991 *Sequences of Proteins of Immunological Interest*, Fifth Edition, U.S. Department of Health and Human Services, NIH Publication No. 91-3242; Tomlinson, I. M. et al., 1992 "The Repertoire of Human Germline $V_H$ Sequences Reveals about Fifty Groups of VH Segments with Different Hypervariable Loops" *J. Mol. Biol.* 227:776-798; and Cox, J. P. L. et al., 1994 "A Directory of Human Germ-line Vκ Segments Reveals a Strong Bias in their Usage" *Eur. J. Immunol.* 24:827-836. Mutagenesis of the germline sequences may be carried out using standard methods, e.g., PCR-mediated mutagenesis where the mutations are incorporated into the PCR primers, or site-directed mutagenesis. If full-length antibodies are desired, sequence is available for the human heavy chain constant region genes; see, e.g., Kabat. E. A. et al., 1991 *Sequences of Proteins of Immunological Interest*, Fifth Edition, U.S. Department of Health and Human Services, NIH Publication No. 91-3242. Fragments containing these regions may be obtained, for example, by standard PCR amplification. Alternatively, the skilled artisan can avail him/herself of vectors already encoding heavy and/or light chain constant regions.

Available techniques exist to recombinantly produce other antibody molecules which retain the specificity of an original antibody. A specific example of this is where DNA encoding the immunoglobulin variable region or the CDRs is introduced into the constant regions, or constant regions and framework regions, of another antibody molecule; see, e.g., EP-184,187, GB 2188638, and EP-239400, and scientific literature in the area. Cloning and expression of antibody molecules, including chimeric antibodies, are described in the literature; see, e.g., EP 0120694 and EP 0125023, and other scientific literature in the area.

Additional antibodies in accordance with the present invention can be raised and then screened for the characteristics identified herein using known techniques. Basic techniques for the preparation of monoclonal antibodies are described in the literature, see, e.g., Kohler and Milstein (1975, Nature 256:495-497). Fully human monoclonal antibodies are produced by available methods. These methods include, but are by no means limited to, the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, full human monoclonal antibodies. This technology is well-known in the art and is fully detailed in various publications, including but not limited to U.S. Pat. Nos. 5,545,806; 5,569,825; 5,625,126; 5,633,425; 5,789,650; 5,877,397; 5,661,016; 5,814,318; 5,874,299; 5,770,249 (assigned to GenPharm International and available through Medarex, under the umbrella of the "UltraMab Human Antibody Development System"); as well as U.S. Pat. Nos. 5,939,598; 6,075,181; 6,114,598; 6,150,584 and related family members (assigned to Abgenix, disclosing their XENOMOUSE® technology). See also reviews from Kellerman and Green, 2002 *Curr. Opinion in Biotechnology* 13:593-597, and Kontermann & Stefan, 2001 *Antibody Engineering*, Springer Laboratory Manuals.

Alternatively, a library of antigen binding fragments in accordance with the present invention may be brought into contact with IL-13Rα1, and ones able to demonstrate binding at the prescribed level, e.g., exhibiting a $K_D$ with the antigen between 1 pM and 200 pM and the ability to antagonize IL-13Rα1-mediated activity selected. Techniques are available to the artisan for the selection of antibody fragments from libraries using enrichment technologies including, but not limited to, phage display (e.g., see technology from Cambridge Antibody Technology (CAT) disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members and/or applications which rely on priority filing GB 9206318, filed May 24, 1992; see also Vaughn et al., 1996, *Nature Biotechnology* 14:309-314), ribosome display (see, e.g., Hanes and Pluckthün, 1997 *Proc. Natl. Acad. Sci.* 94:4937-4942), bacterial display (see, e.g., Georgiou, et al., 1997 *Nature Biotechnology* 15:29-34) and/or yeast display (see, e.g., Kieke, et al., 1997 *Protein Engineering* 10:1303-1310). A library, for example, can be displayed on the surface of bacteriophage particles, with the nucleic acid encoding the antigen binding fragments expressed and displayed on its surface. Nucleic acid may then be isolated from bacteriophage particles exhibiting the desired level of activity and the nucleic acid used in the development of antibody molecules. Individual heavy or light chain clones in accordance with the present invention may also be used to screen for complementary heavy or light chains, respectively, capable of interaction therewith to form a molecule of the combined heavy and light chains; see, e.g., WO 92/01047. Phage display has been described in the literature; see, e.g., Kontermann & Stefan, supra, and WO 92/01047.

Monoclonal antibodies (MAbs) may be purified by techniques available to one of skill in the art. Antibody titers of the relevant ascites, hybridoma culture fluids, or test sample of interest may be determined by various serological or immunological assays which include, but are not limited to, precipitation, passive agglutination, enzyme-linked immunosorbent antibody (ELISA) techniques and radioimmunoassay (RIA) techniques.

In another aspect, the present invention provides a method for antagonizing the activity of IL-13Rα1, which involves contacting a cell expressing IL-13Rα1 with an antibody molecule disclosed herein under conditions that allow said antibody molecule to bind to IL-13Rα1. Specific embodiments of the present invention include such methods wherein the cell is a human cell.

In another aspect, the present invention provides a method for antagonizing the activity of IL-13Rα1 in a subject exhibiting a condition associated with IL-13Rα1 activity, which involves administering to the subject a therapeutically effective amount of an antibody molecule of the present invention. "Antagonizing" herein refers to the act of opposing, counteracting or curtailing one or more functions of the target, be that binding, signaling or other. Inhibition or antagonism of one or more of the IL-13Rα1 functional properties can be readily determined according to methodologies known to the art as well as those described herein. It will, furthermore, be understood that such inhibition or antagonism should effectuate a decrease in the particular activity relative to that seen in the absence of the antibody or, for example, that seen when a control antibody of irrelevant specificity is present. Preferably, an antibody molecule in accordance with the present invention antagonizes IL-13-mediated IL-13Rα1 functioning to the point that there is a decrease of at least 10%, of the measured parameter, and more preferably, a decrease of at least 20%, 30%, 40%, 50%, 60%, 70%, 80%, 90% and 95% of the measured parameter. Such inhibition/antagonism of IL-13Rα1 functioning is particularly effective in those instances where receptor functioning is contributing at least in part to a particular phenotype, disease, disorder or condition which is negatively impacting the subject. Also contemplated are methods of using the disclosed antibody molecules in the manufacture of a medicament for treatment of an IL-13Rα1-mediated disease, disorder or condition.

Antibody molecules disclosed herein may be used in a method of treatment or diagnosis of a particular individual (human or primate). The method of treatment can be prophylactic or therapeutic in nature. In another aspect, the present invention provides a pharmaceutically acceptable composition including an antibody molecule of the invention and a pharmaceutically acceptable carrier, excipient, diluent, stabilizer, buffer, or alternative designed to facilitate administration of the antibody molecule in the desired format and amount to the treated individual. Methods of treatment in accordance with the present invention comprise administering to an individual a therapeutically (or prophylactically) effective amount of an antibody molecule of the present invention. "Therapeutically effective" or "prophylactically effective" amount refers to the amount necessary at the intended dosage to achieve the desired therapeutic/prophylactic effect for the period of time desired. The desired effect may be, for example, amelioration of at least one symptom associated with the treated condition. These amounts will vary, as the skilled artisan will appreciate, according to various factors, including but not limited to the disease state, age, sex and weight of the individual, and the ability of the antibody molecule to elicit the desired effect in the individual. The response may be documented by in vitro assay, in vivo non-human animal studies, and/or further supported from clinical trials. The antibody-based pharmaceutical composition of the present invention may be formulated by any number of strategies known in the art, see, e.g., McGoff and Scher, 2000 *Solution Formulation of Proteins/Peptides*, In: McNally, E. J., ed. Protein Formulation and Delivery. New York, N.Y.: Marcel Dekker; pp. 139-158; Akers & Defilippis, 2000, *Peptides and Proteins as Parenteral Solutions*. In: Pharmaceutical Formulation Development of Peptides and Proteins. Philadelphia, Pa.: Taylor and Francis; pp. 145-177; Akers et al., 2002, *Pharm. Biotechnol.* 14:47-127. A pharmaceutically acceptable composition suitable for patient administration will contain an effective amount of the antibody molecule in a formulation which both retains biological activity while also promoting maximal stability during storage within an acceptable temperature range.

The antibody-based pharmaceutically acceptable composition may be in liquid or solid form. Any technique for production of liquid or solid formulations may be utilized. Such techniques are well within the realm of the abilities of the skilled artisan. Solid formulations may be produced by any available method including, but not limited to, lyophilization, spray drying, or drying by supercritical fluid technology. Solid formulations for oral administration may be in any form rendering the antibody molecule accessible to the patient in the prescribed amount and within the prescribed period of time. The oral formulation can take the form of a number of solid formulations including, but not limited to, a tablet, capsule, or powder. Solid formulations may alternatively be lyophilized and brought into solution prior to administration for either single or multiple dosing. Antibody compositions should generally be formulated within a biologically relevant pH range and may be buffered to maintain a proper pH range during storage. Both liquid and solid formulations generally require storage at lower temperatures (e.g., 2-8° C.) in order to retain stability for longer periods. Formulated antibody compositions, especially liquid formulations, may contain a bacteriostat to prevent or minimize proteolysis during storage, including but not limited to effective concentrations (e.g., ≦1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not limited to polyhydroxy hydrocarbons such as sorbitol, mannitol, glycerol, and dulcitol and/or disaccharides such as sucrose, lactose, maltose, or trehalose) and, in some instances, a relevant salt (including but not limited to NaCl, KCl, or LiCl). Such antibody formulations, especially liquid formulations slated for long term storage, will rely on a useful range of total osmolarity to both promote long term stability at temperatures of, for example, 2-8° C. or higher, while also making the formulation useful for parenteral injection. As appropriate, preservatives, stabilizers, buffers, antioxidants and/or other additives may be included. The formulations may contain a divalent cation (including but not limited to MgCl2, CaCl2, and MnCl2); and/or a non-ionic surfactant (including but not limited to Polysorbate-80 (TWEEN 80™), Polysorbate-60 (TWEEN 60™), Polysorbate-40 (TWEEN 40™), and Polysorbate-20 (TWEEN 20™), polyoxyethylene alkyl ethers, including but not limited to BRIJ 58™, BRIJ 35™, as well as others such as TRITON X-100™, TRITON X-114™, NP40™, Span 85 and the PLURONIC® series of non-ionic surfactants (e.g., PLURONIC® 121). Any combination of such components form specific embodiments of the present invention.

Pharmaceutical compositions in liquid format may include a liquid carrier, e.g., water, petroleum, animal oil, vegetable oil, mineral oil, or synthetic oil. The liquid format may also include physiological saline solution, dextrose or other saccharide solution or glycols, such as ethylene glycol, propylene glycol or polyethylene glycol.

The pharmaceutical composition may be in the form of a parenterally acceptable aqueous solution that is pyrogen-free with suitable pH, tonicity, and stability. Pharmaceutical compositions may be formulated for administration after dilution in isotonic vehicles, for example, Sodium Chloride Injection, Ringer's Injection, or Lactated Ringer's Injection.

Dosing of antibody therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors including but not limited to the antibody molecule utilized, the patient being treated, the condition of the patient, the area being treated, the route of administration, and the treatment desired. A physician or veterinarian of ordinary skill can readily determine and prescribe the effective therapeutic amount of the antibody. Dosage ranges may be from about 0.01 to 100 mg/kg, and more usually 0.05 to 25 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. For purposes of illustration, and not limitation, in specific embodiments, a dose of 5 mg to 2.0 g may be utilized to deliver the antibody molecule systemically. Optimal precision in achieving concentrations of antibody within a range that yields efficacy without toxicity requires a regimen based on the kinetics of the drug's availability to the target site(s). This involves a consideration of the distribution, equilibrium, and elimination of the antibody molecule. Antibodies described herein may be used alone at appropriate dosages. Alternatively, co-administration or sequential administration of other agents may be desirable. It will be possible to present a therapeutic dosing regime for the antibody molecules of the present invention in conjunction with alternative treatment regimes. Individuals (subjects) capable of treatment include primates, human and non-human, and include any non-human mammal or vertebrate of commercial or domestic veterinary importance.

The antibody molecule could be administered to an individual by any route of administration appreciated in the art, including but not limited to oral administration, administration by injection (specific embodiments of which include intravenous, subcutaneous, intraperitoneal or intramuscular injection), administration by inhalation, intranasal, or topical administration, either alone or in combination with other agents designed to assist in the treatment of the individual. The route of administration should be determined based on a number of considerations appreciated by the skilled artisan including, but not limited to, the desired physiochemical characteristics of the treatment. Treatment may be provided on a daily, weekly, biweekly, or monthly basis, or any other regimen that delivers the appropriate amount of antibody molecule to the individual at the prescribed times such that the desired treatment is effected and maintained. The formulations may be administered in a single dose or in more than one dose at separate times.

In particular embodiments, the condition treated is selected from the group consisting of: asthma, allergy, allergic rhinitis, chronic sinusitis, hay fever, atopic dermatitis, chronic obstructive pulmonary disease ("COPD"), pulmonary fibrosis, esophageal eosinophilia, psoriasis, psoriatic arthritis, fibrosis, scleroderma, inflammatory bowel disease (particularly, ulcerative colitis), anaphylaxis, and cancer (particularly, Hodgkin's lymphoma, glioma, and renal carcinoma), and general Th2-mediated disorders/conditions. Use of an antibody molecule, therefore, in the manufacture of a medicament for treatment of an IL-13Rα1-mediated condition, including those specified above, therefore, forms an important embodiment of the present invention.

The present invention further provides for the administration of the disclosed anti-hIL-13Rα1 antibody molecules for purposes of gene therapy. In such a method, the cells of a subject would be transformed with nucleic acid encoding the antibody molecules of the invention. Subjects comprising the nucleic acids will then produce the antibody molecules endogenously. Previously, Alvarez, et al, *Clinical Cancer Research* 6:3081-3087, 2000, introduced single-chain anti-ErbB2 antibodies to subjects using a gene therapy approach. The methods disclosed by Alvarez, et al, may be easily adapted for the introduction of nucleic acids encoding an anti-hIL-13Rα1 antibody of the invention to a subject.

Nucleic acids encoding any polypeptide or antibody molecule of the invention may be introduced to a subject. In specific embodiments, the antibody molecule is a human, single-chain antibody.

The nucleic acids may be introduced to the cells of a subject by any means known in the art. In specific embodiments, the nucleic acids are introduced as part of a viral vector. Examples of specific viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, AVIGEN, Inc. (Alameda, Calif.; AAV vectors), Cell Genesys (Foster City, Calif.; retroviral, adenoviral, AAV vectors, and lentiviral vectors), CLONTECH (retroviral and baculoviral vectors), Genovo, Inc. (Sharon Hill, Pa.; adenoviral and AAV vectors), GENVEC (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). In specific embodiments, the viral vectors are replication defective, that is, they are unable to replicate autonomously, and thus are not infectious, in the target cell. The replication defective virus may be a minimal virus, i.e., it retains only the sequences of its genome which are necessary for encapsidating the genome to produce viral particles. Defective viruses, which entirely or almost entirely lack viral genes, may also be used as well. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno et al, *Cancer Gen. Ther.* 6:147-154, 1999; Kaplitt et al, *J. Neurosci. Meth.* 71:125-132, 1997 and Kaplitt et al, *J. Neuro One.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992 are desirable in some instances. Various replication defective adenovirus and minimum adenovirus vectors have been described (WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al, *Gene Ther.* 8:1343-1346, 2001, Larson et al, *Adv. Exp. Med. Bio,* 489:45-57, 2001; WO 91/18088 and WO 93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.*, 62:1120, 1988; EP 453242 and EP178220. The retroviruses are integrating viruses which infect dividing cells.

Lentiviral vectors can be used as agents for the direct delivery and sustained expression of nucleic acids encoding an antibody molecule of the invention in several tissue types, including brain, retina, muscle, liver and blood. The vectors can efficiently transduce dividing and nondividing cells in these tissues, and maintain long-term expression of the antibody molecule. For a review, see Zufferey et al, *J. Virol.* 72:9873-80, 1998 and Kafri et al, *Curr. Opin. Mol. Ther.* 3:316-326, 2001. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than 106 IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus et al, *Microbiol. Rev.,* 58:491-562, 1994; Bredenbeek et al, *J. Virol.,* 67:6439-6446, 1993; Ijima et al, *Int. J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for gene therapy has been described. (Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in PCT Publication Nos. WO 95/18863 and WO 96/17823, and in U.S. Pat. No. 5,459,127.

It is also possible to introduce the vector in vivo as a naked DNA plasmid. Naked DNA vectors for gene therapy can be introduced into the desired host cells by methods known in the art, e.g., electroporation, microinjection, cell fusion, DEAE-dextran, calcium phosphate precipitation, use of a gene gun, or use of a DNA vector transporter (see, e.g., Wilson, et al, *J. Biol, Chem.* 267:963-967, 1992; Williams et al, *Proc. Natl. Acad. Sci. USA* 88:2726-2730, 1991). Receptor-mediated DNA delivery approaches can also be used (Wu et al, *J. Biol. Chem.* 263:14621-14624, 1988). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, *Bioelectrochemistry* 53:1-10, 2001; PCT Publication Nos. WO 99/01157, WO 99/01158 and WO 99/01175).

Pharmaceutical compositions suitable for such gene therapy approaches and comprising nucleic acids encoding an anti-hIL-13Rα1 antibody molecule of the present invention are included within the scope of the present invention.

In another aspect, the present invention provides a method for identifying, isolating, quantifying or antagonizing IL-13Rα1 in a sample of interest using an antibody molecule of the present invention. The antibody molecules may be utilized as a research tool in immunochemical assays, such as Western blots, ELISAs, radioimmunoassay, immunohistochemical assays, immunoprecipitations, or other immunochemical assays known in the art (see, e.g., Immunological Techniques Laboratory Manual, ed. Goers, J. 1993, Academic Press) or various purification protocols. The antibody molecules may have a label to facilitate ready identification or measurement of the activities associated therewith. One skilled in the art is readily familiar with the various types of detectable labels (e.g., enzymes, dyes, or other suitable molecules which are either readily detectable or cause some activity/result that is readily detectable) useful in the above protocols.

An additional aspect of the present invention are kits including the antibody molecules or pharmaceutical compositions disclosed herein and instructions for use. Kits typically but need not include a label indicating the intended use of the contents of the kit. The term "label" includes any writing, or recorded material supplied on or with the kit, or which otherwise accompanies the kit.

The invention is described in greater detail by the following non-limiting examples.

EXAMPLE 1

Production and Purification of a Recombinant Protein Based on the Human IL-13Rα1Extracellular Region Using the protocol described herein, an N-terminal FLAG®-tagged fusion protein encompassing most of the extracellular region of human IL-13Rα1 (amino acids number 3 to 317 of SEQ ID NO:81) was purified from culture media conditioned by a stably transfected (pEFBOS-S-FLAG® vector encoding IL-13Rα1 ECR) CHO cell clone.

The purified hIL-13Rα1.ECR protein (SEQ ID NO:82) was concentrated and subsequently desalted into phosphate-buffered saline (PBS), 0.02% v/v TWEEN™ 20, followed by filter sterilization. Typical recovery was 0.4 mg protein per liter of conditioned media. Protein was stored at −80° C. until required.

Methods. A pEFBOS-S-FLAG® expression vector, incorporating a cDNA encoding the extracellular region (ECR) of human IL-13Rα1 with an IL-3 signal sequence and FLAG®-tag fusion, was transfected into CHO cells for stable expression using standard procedures. CHO-derived conditioned media was then concentrated 10-fold by ultrafiltration using a 10-kDa cut-off membrane. Concentrated media was applied to an M2 (anti-FLAG®) affinity chromatography column and eluted with FLAG® peptide at a concentration of 100 μg/ml. The eluate was concentrated by lyophilization and then buffer exchanged into Tris pH 8.0 using GF50 SEPHAROSE™ resin packed into column (2.6 cm×40 cm). The buffer exchanged fraction was then subjected to anion exchange chromatography using a MONO™ Q 5/5 column. A proteolyzed fragment of IL-13Rα1 was strongly retained and was separated from the full-length IL-13Rα1 which eluted at a lower salt concentration. Pooled fractions and filter sterilized final product was assessed by SDS-PAGE and western blot analysis. The sample was then quantitated using UV absorbance where 1 absorbance unit was approximately 1 mg/ml.

EXAMPLE 2

Generation of Hybridoma Cell Lines Producing Human Anti-Human IL-13Rα1 Monoclonal Antibodies Immunization of Transgenic Mice. Male and female transgenic mice from the HCo7, HCo12 and HCo7xHCo12 strains (HUMAB™ mice, Medarex, USA) were immunized with hIL-13Rα1.ECR of Example 1. For the first immunization, 20-50 μg of hIL-13Rα1.ECR was emulsified in Complete Freund's Adjuvant (CFA) and administered via the intraperitoneal (i.p.) route. For a minimum of two and a maximum of three subsequent i.p. immunizations, 20-50 μg of hIL-13Rα1.ECR was emulsified in Incomplete Freund's Adjuvant (IFA). Following the second or third immunization with hIL-13Rα1.ECR in IFA, serum was sampled (retro-orbital plexus) and assayed for human antibodies against the hIL-13Rα1. ECR by ELISA as described herein. High-responder mice (serum titers generally >1:3200) were selected for hybridoma generation. In some cases, animals not used for hybridoma generation at this point received further i.p. immunizations with 20-50 μg of hIL-13Rα1.ECR in PBS. Serum from these animals was again assayed for human antibodies against the hIL-13Rα1.ECR by ELISA and high-responder mice were used for hybridoma generation. Mice selected for hybridoma generation were boosted intravenously with 20-50 μg of hIL-13Rα1.ECR 3-4 days prior to spleen cell fusion.

Antigen-Specific ELISA. Mouse serum or hybridoma culture supernatant fluid (SNF) was assessed for mabs able to bind to plate bound hIL-13Rα1.ECR using a standard ELISA format as follows. Flat bottom 96-well MAXISORP™ plates (NUNC, Invitro Technologies, #439-454) were coated with 50 μl of a solution containing 2.5 μg/ml hIL-13Rα1.ECR diluted in PBS, overnight at 4° C. After washing two times with PBS plates are blocked with 2% w/v skim milk in PBS (blocking buffer, 200 μl/well) for 1 hour, 37° C. then washed a further two times with PBS containing 0.1% v/v TWEEN™ 20 (wash buffer). Fifty μl of test hybridoma SNF or mouse serum was added per well and plates were incubated at room temperature for 1 hour. Plates were washed three times. Bound human mAbs were detected using an anti-human IgG HRP-conjugated secondary reagent diluted 1:1000 in PBS containing 1% w/v skim milk powder and 0.1% v/v TWEEN™ 20. Fifty μl/well of the anti-human IgG HRP-conjugated secondary reagent was added to the plates for 1 hour at room temperature. The plates were then washed three times, developed with TMB substrate, and read OD at 450 nm.

Hybridoma Generation. Selected high-responder mice were sacrificed and the spleen and relevant lymph nodes were collected. The fusion of spleen and lymph node cells with the fusion partner SP2/O and subsequent HAT (hypoxanthine/aminopterin/thymidine) (GIBCO-BRL, #21060-017) selection of hybridomas was performed according to standard procedures (Antibodies: A Laboratory Manual: Harlow and Lane. Cold Spring Harbor Laboratory Press). Briefly, the centrifuge was adjusted to room temperature, with a water-bath to 37° C. and a heat block to 37° C. Polyethylene glycol (PEG) was warmed to 37° C. Medium was prepared for culturing cells after the fusion was completed. The medium was hybridoma serum-free medium (HSFM) (GIBCO-BRL, #12045-084) with 5% Ultra low IgG FBS (FBS) (GIBCO-BRL, #16250-078), 2 mM GLUTAMAX®-1 (GIBCO-BRL, #35050-061), 50 U/50 μg/ml Penicillin/Streptomycin (GIBCO-BRL, # 15070-063) and 1×HAT. Media was warmed to 37° C. SP2/O cells were harvested and a viable cell count was performed. The cells were healthy, actively dividing and in log-phase. The viability was >95%. SP2/Os were cultured in HSFM/5% Ultra low IgG FBS prior to fusion, and split 1:2 or 1:3 on the day before the fusion. On the day of fusion, the animals were sacrificed and the spleen (and lymph nodes if required) were immediately removed into sterile medium (Dulbecco's modification of Eagles media (GIBCO-BRL, #11995-073) or DME) on ice. A single cell suspension was prepared from the spleen, and washed twice (1800 rpm for 7 minutes) in DME, the second wash warm. The SP2/O cells were washed three times (1500 rpm, 7 minutes) with warm DME to remove all traces of serum. SP2/O cells ($10^8$) were used for one mouse spleen, done as two separate fusions. SP2/O cells and spleen cells were pooled together in the same tube and centrifuged at 2100 rpm (400 g) for 5 minutes. All DME was removed, leaving only combined pellet. The DME was placed in 37° C. heat block. One ml of warm PEG was added drop-wise to the cell pellet over 1 minute whilst stirring the pellet gently with the pipette. Stirring continued gently for another minute. One ml warm DME was added, drop-wise, stirring, over 1 minute. Another 1 ml DME was added over 1 minute. Then 20 ml DME was added over 5 minutes while stirring slowly. This was then centrifuged for 5 minutes at 1500 rpm. All supernatant was removed, and cells were resuspended gently in culture medium as above. One mouse spleen was plated to 5 microtiter plates at 0.2 ml per well in HAT medium. The plates were fed by removing approximately 0.1 ml from each well and replacing with fresh HAT medium every 3 or 4 days. Wells were checked for growth of hybridomas at day 7-10 (routine screening 10-14 days after the fusion). Being sure that the medium had not been changed for at least 2-3 days beforehand, ~100 μl of supernatant was removed from each well for assay. Positives were transferred to 1 ml or 2 ml wells then gradually expanded to 6-well plates. Hybridomas were not clonal at this stage. After 14 days in HAT medium, hybridomas were cultured in HT (GIBCO-BRL, #11067-030) (HSFM, 5% Ultralow IgGFBS, 10 ng/ml rhIL-6 (R&D Systems, #206-IL-050) and HT) for approximately 2 more weeks then without HT.

Culture of Hybridomas. Hybridomas testing positive at primary and follow-up confirmation ELISA screens were cloned by limit dilution. Limit dilution wells containing single colonies were screened by ELISA and a positive well was selected for expansion. Further rounds of limit dilution cloning were carried out until 100% of wells test positive.

For production of supernatant fluid (SNF) for antibody purification, hybridomas were expanded into either T175 cm$^2$ flasks (FALCON, #3028) or roller bottles (900 cm$^2$) (CORNING, #430849). Media used for generation of hybridoma SNFs was HSFM supplemented with 5% Ultralow IgG FBS, 2 mM glutamine and 50 U/50 µg/ml penicillin/streptomycin. Hybridomas were allowed to grow to confluence and media was harvested by centrifugation approximately 5-10 days later when >90% of cells were dead. All conditioned media was filtered using a STERICUP™ filter apparatus (MILLIPORE, #SCGPUllRE) (0.45 µm) prior to mAb purification.

Production of Purified mAbs. Monoclonal antibodies were purified from SNF using a standard Protein A affinity chromatography-based strategy, using, e.g., the following reagents. HPLC: AKTA explorer (AMERSHAM Biosciences, Sweden); Column: Protein A (HITRAP™-1 ml, AMERSHAM Biosciences, Sweden); Buffer A: PBS, 0.02% TWEEN™ 20; Buffer B: 0.1 M Glycine pH 2.8; Buffer C: 2 M Tris pH 8.0.

The column was prepared by washing with 5 volumes of buffer A. Conditioned media was loaded onto dedicated column. A wash was performed with 100 volumes of buffer A, and elution with 20 ml (10×2 ml) of buffer B. Collection was into tube containing 0.2 ml of buffer C. Column was washed with buffer A to store at 4° C. Desalting was performed using 10 K cut-off dialysis membrane into PBS, 0.02% TWEEN™ 20. mAb purity was demonstrated by SDS-PAGE with COOMASSIE® Blue staining.

Antibody was quantitated by spectrophotometric analysis at 280 nm using an immunoglobulin extinction coefficient of 1.0 absorbance unit being equivalent to 1.34 mg/ml of antibody.

EXAMPLE 3

Analysis of Anti-Human Il-13Rα1 Monoclonal Antibodies 2B6, 4A10, 6C11 and 8B4

BIACORE-Based Studies. Human IL-13Rα1.ECR (40 µg/ml in 20 mM Sodium Acetate, pH 4.2) of Example 1 was immobilized to a sensorchip (CM5, Biosensor, Sweden) using standard NHS/EDC chemistry according to the manufacturer's instructions at a set immobilization value, for example, 1000RU. Ethanolamine (1.0 M) pH 8.0 was used to quench residual active esters post hIL-13Rα1.ECR immobilization.

Analysis of binding of antibody (concentration range of 1.4 nM to 150 nM, two-fold dilutions) to the immobilized hIL-13Rα1. ECR was performed in duplicate. Sensorgrams generated were fitted to a bivalent ligand binding model to simultaneously derive association ($k_a$) and dissociation ($k_d$) rates and used to determine binding affinity ($K_D$, Biaevaluation software, BIACORE™, Sweden).

Normal Human Dermal Fibroblast (NHDF) Eotaxin Assay. NHDF cells were purchased from Cambrex (#CC-2509) and were cultured in FGM media (Cambrex CC3132) supplemented with additives provided, referred to below as complete media. Cells were passaged 1:3 or 1:5 once a week and were monitored for responsiveness to IL-13 prior to using. To assess antagonistic activity of IL-13Rα1 antibodies, cells were resuspended to 2×10$^6$/ml in complete media containing 20 ng/ml PMA (SIGMA P8139) and 20 µg/ml polymyxin (SIGMA #P4932) and plated in 96 well flat bottom plates (COSTAR #3595) at 1×10$^5$ cell/well. Antibody titrations were added to the cells and incubated for 30 minutes, at 37° C. in a 5% CO$_2$ incubator. Recombinant rhesus IL-13 was added at 10 ng/ml final concentration and plates incubated overnight at 37° C. in a 5% CO$_2$ incubator. Supernatants were removed and assayed for eotaxin content by immunoassay, as follows. IMMULON®-4 plates (DYNATECH #3855) were coated with 2 µg/ml anti-human eotaxin antibody (PHARMINGEN #555035) in PBS (INVITROGEN, #14190-144), overnight at 4° C. The plates were blocked with blocking buffer for 1 hour at room temperature and washed three times with wash buffer. Supernatants from the NHDF cells were added to the plates along with a recombinant human eotaxin standard (R&D Systems, #320-EO). The samples were captured for 2 hours at room temperature, washed and biotinylated anti-human Eotaxin detection antibody (PHARMINGEN, #555060) was added at 200 ng/ml for 1 hour at room temperature. Plates were washed and streptavidin-europium (Wallac, #1244-360) was added at a concentration of 100 ng/ml for 20 minutes at room temperature. A final wash step was performed and enhancement solution (Wallac, #1244-105) was added for 1 hour at room temperature. Plates were read by time-delayed fluorescence on a VICTOR (PERKIN-ELMER) plate reader.

Results. Antibodies were tested for their ability to antagonize IL-13Rα1-mediated activity in the NHDF assay. Antibodies selected as having comparatively good binding in the ELISA assay and as antagonists of IL-13 in the NHDF assay were 2B6, 4A10, 6C11 and 8B4. Binding to chip bound hIL-13Rα1 extracellular domain was assessed by BIACORE™ analysis. The results for each of these assays are summarized in Table 2.

TABLE 2

| Antibody | ELISA ($K_D$) (pM) | NHDF cells IL-13 Eotaxin release ($IC_{50}$) (µg/ml) [on average] | $K_D$ (nM) BIACORE ™ |
|---|---|---|---|
| 2B6 | 360 | 3.5 | 16.5 |
| 4A10 | 1200 | 0.35 | 5.8 |
| 6C11 | 87 | 9.7 | 2.1 |
| 8B4 | 267 | 1.0 | 4.6 |

Variable heavy and light chain sequences were cloned from mRNA isolated from the hybridoma cell line expressing antibodies 2136, 4A10, 6C11 and 8B4. 6C11 and 8B4 have the same light chain variable region sequence, and there are only three amino acid differences in the heavy chain variable region sequences.

Hybridomas expressing 236, 6C11 and 8B4 were deposited with the ATCC as follows: 2B6 under PTA-6932; 6C11 under PTA-6930; and 8B4 under PTA-6934.

The CDR regions of 2B6, 4A10, 6C11 and 8B4 are delineated using the Kabat system (Kabat et al, Sequences of Proteins of Immunological Interest, Fifth Edition, U.S. Department of Health and Human Services, NIH Publication No. 91:3242, 1991), except for $V_H$ CDR1, which is extended to encompass both sequence and structural (Chothia and Lesk, J. Mol. Biol. 196:901-917, 1987) definitions, viz. $V_H$ residues 26-35.

EXAMPLE 4

Functional Studies—STAT6 Phosphorylation

NHDF IL-13-Induced STAT6 Phosphorylation Assay. NHDF cells were purchased from Cambrex (#CC-2509) and were cultured in FGM media (Cambrex CC3132) supplemented with additives provided. NHDF cells were plated at 2e6/ml in 50 µl volume in 96-well V-bottom polypropylene PCR plates (#1442-9596, USA scientific) in RPMI Media (#22400-071, INVITROGEN). Anti-IL13R antibodies were added in 25 µl volume and incubated for 30 minutes at 4° C. Recombinant rhesus IL-13 was added at 100 ng/ml final concentration. The plates were warmed to 37° C. in a PCR machine for 20 minutes and, immediately, equal volume of 2× lysis buffer (100 µl) was added. pSTAT6 was measured by immunoassay. IMMULON®-4 plates (#3855, DYNATECH) were coated with anti-human phospho STAT6 (621995, BD Transduction Labs) at 10 µg/ml in PBS (#14290-144, INVITROGEN) (50 µl/well) overnight at 4° C. Blocking buffer (200 µl/well) was added for 1 hour at room temperature. The plates were washed three times with wash buffer. Fifty µl/well lysate was added and incubated for 2 hours at room temperature. The plates were washed three times with wash buffer. Detection was enabled with biotin anti-STAT6 (621141, BD Transduction Labs conjugated 20:1 molar ratio) at 2 µg/ml in blocking buffer (60 µl/well) added for 1 hour at room temperature. The plates were washed three times with wash buffer. Streptavidin-Europium (#1244-360, Wallac) (100 µl/well) at 100 ng/ml was added in europium buffer for 20 minutes at room temperature. The plates were washed three times with wash buffer. Enhancement solution (#12244-105, Wallac) (150 µl/well) was added for 1 hour at room temperature, and plates were read by time-delayed fluorescence on a VICTOR (PERKIN-ELMER) reader.

Results. The $EC_{50}$ for 2B6 was determined to be 7.0 µg/ml. The $EC_{50}$ for 8B4 averaged at ~2.9 µg/ml. The $EC_{50}$ for 6C11 was determined to be 3.8 µg/ml.

EXAMPLE 5

Functional Studies—Tarc Release

Thymus and Activation-Regulated Chemokine (TARC) Release Assay (Dog, Rhesus or Human). Blood was collected in heparinized VACUTAINER™ tubes (VT6480, VWR). PBMCs were isolated over Lymphocyte Separation Media (ICN, 50494X). PBMCs or whole blood was plated in 96 well flat bottom plates (#2595, COSTAR). Antibodies were added and plates incubated for 30 minutes at room temperature. Recombinant rhesus IL-13 was added at 10 ng/ml final concentration and plates incubated for 24-72 hours at 37° C. with $CO_2$ in a humidified chamber. Supernate or plasma was collected (TARC can be detected as early as 24 hours but levels continue to increase). TARC was measured by immunoassay. IMMULON®-4 plates (#3855, DYNATECH) were coated with anti-human TARC (R&D #AF364) at 2 µg/ml in PBS (#14290-144, INVITROGEN) (50 µl/well). The plates were incubated overnight at 4° C. Blocking buffer (200 µl/well) was added and incubated for 1 hour at room temperature. The plates were washed three times with wash buffer. Plasma or supernate was added, 50 µl/well, and incubated for 2 hours at room temperature (plasma diluted 1:2). A standard curve was included starting at 20 ng/ml recombinant human TARC diluted 2-fold. The plates were washed three times with wash buffer. Detection was carried out with biotin anti-human TARC(RDI, #RDI-TarcabrP1 conjugated to biotin 20:1 molar ratio) at 250 ng/ml in blocking buffer (60 µl/well) for 1 hour at room temperature. The plates were washed three times with wash buffer. Streptavidin-Europium (#1244-360, Wallac) was added, 100 µl/well, at 100 ng/ml in europium buffer for 20 minutes at room temperature. The plates were washed three times with wash buffer. Enhancement solution (#12244-105, Wallac), 150 µl/well, was added and incubated for 1 hour at room temperature. Time-delayed fluorescence was read in a VICTOR (PERKIN-ELMER) reader.

Results. 8B4 yielded an $IC_{50}$ on average of ~2.6 µg/ml. 6C11 yielded an $IC_{50}$ of 2.50 µg/ml.

EXAMPLE 6

Optimization of 8b4

The variable heavy and variable light sequences of 8B4 were cloned in a Fab phage-display vector, pFab3d (FIG. 1) with a 1929 bp XhoI/ApaI fragment from the PKS3 locus of the fungus *Glarea lozoyensis* cloned at the XhoI/ApaI site as a stuffer in the light chain construct, then randomly mutated in the variable heavy and light CDR3 sequences (each library possessing >$10^8$ functional diversity). The resultant mutants were then panned against biotinylated human and primate (rhesus and cynomologous monkey) IL-13Rα1 in solution using standard phage display protocols (see, e.g., *Phage Display: A Laboratory Manual*, 2001, Cold Spring Harbor Laboratory Press). Human and primate sequences have been disclosed in the literature; see, e.g., Accession Nos: U62858, CAA70508, and AAP78901. By lowering the concentration of target in each subsequent round of panning (e.g., 10 nM, 1 nM, 0.1 nM, and 0.01 nM), the stringency of panning was effectively increased, thereby enriching for higher and higher affinity phage with each subsequent round. Phage ELISA was used as the primary assay to determine the ability of the phage-bound recombinant Fabs to recognize the biotinylated IL-13Rα1immobilized on streptavidin plates (see, e.g., Phage Display: A Laboratory Manual, supra). Myc-capture ELISA and dissociation assays (general protocols described below) were used as secondary screening tools. BIACORE™ surface plasmon resonance and/or KINEXA™ kinetic exclusion assays were run to characterize the binding kinetics of the antibodies identified. These assays were conducted in accordance with the published manufacturers' protocols and binding kinetics determined in the usual manner. Specific antibodies were converted into full-length antibodies of subclass IgG4 for expression, production and characterization in mammalian cells (general protocol described herein).

Myc Capture and Dissociation Assays. Two assays are conducted in parallel. The first (I) measured the amount of antibody captured from peripreps. This assured that data was collected only from wells that had sufficient and equivalent amounts of antibody. The second (II) measured the dissociation of IL-13 receptor from the plate-bound antibody.

Assay (I): IMMULON®-4 plates (DYNATECH #3855) were coated with polyclonal anti-human kappa antibody (Immunology Consultants Lab #GKBF-80A-K116), 5 µg/ml in PBS (#14290-144, INVITROGEN), 50 µl/well and incubated overnight at 4° C. Blocking buffer (200 µl/well) was added and the plates were incubated for 1 hour at room temperature. The plates were washed three times with wash buffer. Neat periprep was added, 50 µl/well, and left for 2 hours at room temperature. The plates were washed three times with wash buffer. Fifty µg/ml of human gamma globulin (Pierce #31879) was added in block buffer and left to incubate overnight at 4° C. The plates were washed three times with wash buffer in the morning and afternoon followed by the addition of 150 µl/well of block buffer while incubating at 37° C. throughout. The plates were washed three times with wash buffer. Bound antibody was detected with biotin anti-Myc (Upstate #16-212) at 1 µg/ml in blocking buffer (60 µl/well) for 1 hour at room temperature. The plates were washed three times with wash buffer. Streptavidin-europium (Wallac,

1244-360) was added, 100 μl/well, at 100 ng/ml in Europium buffer, for 20 minutes at room temperature. A final wash step (three times) was performed and enhancement solution (Wallac, #1244-105), 150 μl/well, was added for 1 hour at room temperature. Plates were read by time-delayed fluorescence on a VICTOR (PERKIN-ELMER) plate reader.

Assay (II): IMMULON®-4 plates (DYNATECH, #3855) were coated with polyclonal anti-human kappa antibody (Immunology Consultants Lab #GKBF-80A-K116), 5 μg/ml in PBS (#14290-144, INVITROGEN) (50 μl/well), and incubated overnight at 4° C. Blocking buffer (200 μl/well) was added and the plates were incubated for 1 hour at room temperature. The plates were washed three times with wash buffer. Neat periprep was added, 50 μl/well, and left for 2 hours at room temperature. The plates were washed three times with wash buffer. Sixty μl/ml of 400 ng/ml FLAG®-tagged human IL-13 receptor was added with 50 μg/ml of human gamma globulin (Pierce #31879) in block buffer and left to incubate overnight at 4° C. The plates were washed three times with wash buffer in the morning and afternoon followed by the addition of 150 μl/well of block buffer while incubating at 37° C. throughout. The plates were washed three times with wash buffer. Residual IL-13 receptor was detected with biotin anti-FLAG® (IBI, #3081/6H2411) at 1 μg/ml in blocking buffer (60 μl/well) for 1 hour at room temperature. The plates were washed three times with wash buffer. Streptavidin-europium (Wallac, #1244-360) was added, 100 μl/well at 100 ng/ml in Europium buffer, for 20 minutes at room temperature. A final wash step (three times) was performed and enhancement solution (Wallac, #1244-105), 150 μl/well, was added for 1 hour at room temperature. Plates were read by time-delayed fluorescence on a Victor (Perkin-Elmer) plate reader.

Conversion to Full-Length IgGs. Anti-IL-13 μl monoclonal antibodies were converted into whole antibody of subclass IgG4 for expression and production in mammalian cells. Their variable regions were PCR amplified from the corresponding Fab vectors and in-frame cloned into a LONZA pCON antibody expression vector with leader sequences in front of the antibody sequences. In the vector, genomic DNA sequences for all constant regions for light and heavy chains were already engineered in the vectors. The expression is driven by a human cytomegalovirus (CMV) early promoter and followed by an SV40 polyadenylation signal. The plasmids have bacterial sequence for plasmid replication and ampicillin selection marker and the plasmid for the light chain, pCONKAPPA, has the GS gene for glutamine synthetase as a selection marker in mammalian cells. In-frame fusion of variable regions allows the proper expression of whole antibody. By design, leader sequences from mouse light and heavy chains were included in front of the antibody open reading frames. A consensus Kozak sequence (italics only) was also included surrounding the ATG start codon to improve protein expression level. Forward and reverse primers were designed for PCR amplification: light chain variable region forward primer: 5'-ATC GAAGCTTGC CGC CAC C ATGAGTGTGCCCACTCAGGTCCTGGGGTTGCTGCTGCTGT AAT TGT GCT GAC TCA GTC T-3' (SEQ ID NO:59) and reverse primer 5'-CCA CCGTACGTT TGA TTT CCA C-3' (SEQ ID NO:60); heavy chain variable region forward primer 5'-GCA CTG AAGCTTGCC GCC ACC ATGGAATGGAGCTGGGTCTTTCTCTTCTTCCTGTCAGTAACTACAGGTGTCCACTCCGAG GTG CAG GTG TTG GAG TCT-3' (SEQ ID NO:61) and reverse primer 5'-AGA CCG ATGGGCCCT TGG TGG AGG CT-3' (SEQ ID NO:62). The leader sequences in the forward primers are bolded and underlined and cloning sites (HindIII in the forward primers for both light and heavy chains, BsiwI in the reverse primer for the light chain, and ApaI in the reverse primer for the heavy chain) are given in underlining and italics.

The variable regions were PCR amplified for 20 cycles using these pairs of primers using Fab vectors carrying 8B4 variable region sequences. PCR products were digested with HindIII and BsiWI for light chains and HindIII and ApaI for heavy chains. Enzyme-digested PCR fragments were cloned into Lonza's vectors (pCONKAPPA for light chain and pCONGAMMA4 for heavy chain). The entire expression cassette of respective heavy chain from pCONGAMMA4 vectors digested with NotI and SalI was then inserted into the corresponding light chain vector digested with the same enzymes. The entire open reading frames for both light chain and heavy chain were verified by DNA sequencing.

Antibody Expression, Purification and Characterization. Either combined light chain and heavy chain plasmid DNA or a 1:1 ratio mixture of corresponding light and heavy chain plasmid DNA were transfected in 293-derived cell lines. For pCON vectors, 293 FREESTYLE™ suspension cell line from INVITROGEN was used along with its transfection reagents. For 200 ml of 293 FREESTYLE™ cells, 100 μg each of heavy and light chain plasmid DNA and 300 μl of transfection reagent were used for transfection. The transfected cells were incubated at 37° C./5% $CO_2$ for 7-8 days before harvest. Culture medium was harvested, filtered and concentrated using by low speed MILLIPORE CENTRICON™ centrifugation (concentrator, MilliPore).

Results. KINEXA® analyses were performed on select antibodies. The data for specific full-length antibodies as IgG4s is provided in Table 3:

TABLE 3

| Antibody | VHCDR3 | VLCDR3 | $K_D$ (pM) |
|---|---|---|---|
| 8B4-IgG4 | SEQ ID NO: 23 | SEQ ID NO: 20 | 680 |
| 8B4-78M-IgG4 | SEQ ID NO: 23 | SEQ ID NO: 24 | 38 |
| 8B4-18C-IgG4 | SEQ ID NO: 23 | SEQ ID NO: 26 | 51 |

Binding to chip bound hIL-13Rα1 extracellular domain was assessed by BIACORE™ analysis for various antibodies in Fab format. The results of this analysis are provided in Table 4.

TABLE 4

| Antibody (Fab) | VHCDR3 | VLCDR3 | $K_D$ (pM) |
|---|---|---|---|
| 8B4 (Fab) | SEQ ID NO: 23 | SEQ ID NO: 20 | 2150 (ave.) |
| 8B4-78M (Fab) | SEQ ID NO: 23 | SEQ ID NO: 24 | 49 (ave.) |
| 8B4-82 (Fab) | SEQ ID NO: 23 | SEQ ID NO: 25 | 73 |
| 8B4-18C (Fab) | SEQ ID NO: 23 | SEQ ID NO: 26 | 85 |
| 8B4-36 (Fab) | SEQ ID NO: 23 | SEQ ID NO: 27 | 85 |
| 8B4-21C (Fab) | SEQ ID NO: 23 | SEQ ID NO: 28 | 170 |
| 8B4-74C (Fab) | SEQ ID NO: 23 | SEQ ID NO: 29 | 45 |
| 8B4-80C (Fab) | SEQ ID NO: 23 | SEQ ID NO: 63 | 250 |

The data demonstrate the identification, through various screens and analyses conducted, antibodies with significantly enhanced affinity for hIL-13Rα1.

EXAMPLE 7

Functional Studies—Eotaxin Release of Optimized Antibody

In accordance with the method of Example 3, the $IC_{50}$ for 8B4-IGg4 and the optimized antibody 8B4-78M derived from 8B4 for inhibition of eotaxin release from NHDF cells upon stimulation with IL-13 were ~1 µg/ml and ~0.1 µg/ml, respectively. In addition, the $IC_{50}$ values for 8B4-74C, 8B4-36, 8B4-82, and 8B4021C were, respectively, 0.10 µg/ml, 0.17 µg/ml, 1.31 µg/ml, and 0.75 µg/ml.

What is claimed is:

1. An isolated antibody that binds to human interleukin 13 receptor alpha 1, wherein
   (a) the heavy chain variable region of said antibody comprises CDR1, CDR2 and CDR3 amino acid sequences as set forth in SEQ ID NOs:22, 15 and 23, respectively; and
   (b) the light chain variable region of said antibody comprises CDR1, CDR2 and CDR3 sequences as set forth in:
      (i) SEQ ID NOs:18, 19 and 24, respectively;
      (ii) SEQ ID NOs:18, 19 and 27, respectively; or
      (iii) SEQ ID NOs:18, 19 and 29, respectively,
   wherein the antibody has a $K_D$ for the interaction of the antibody with hIL-13Rα1 of less than 100 pM, and wherein the antibody antagonizes interleukin 13-induced human interleukin 13 receptor alpha 1-mediated eotaxin release from NHDF cells.

2. The isolated antibody of claim 1, further comprising a heavy chain constant region as set forth in SEQ ID NO:79.

3. A composition comprising the antibody of claim 1 and a pharmaceutically acceptable carrier.

4. An isolated nucleic acid encoding an antibody of claim 1.

5. An isolated vector comprising the nucleic acid of claim 4.

6. An isolated host cell comprising the vector of claim 5.

* * * * *